US011974837B2

(12) United States Patent
Mizuno et al.

(10) Patent No.: US 11,974,837 B2
(45) Date of Patent: May 7, 2024

(54) BLOOD PRESSURE MEASUREMENT DEVICE

(71) Applicants: OMRON CORPORATION, Kyoto (JP); OMRON HEALTHCARE CO., LTD., Muko (JP)

(72) Inventors: Shinji Mizuno, Yasu (JP); Noboru Kohara, Okayama (JP); Hirokazu Tanaka, Otsu (JP); Tomoyuki Nishida, Kyoto (JP); Takashi Ono, Kyoto (JP); Takanori Nishioka, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 899 days.

(21) Appl. No.: 16/926,079

(22) Filed: Jul. 10, 2020

(65) Prior Publication Data
US 2020/0337565 A1     Oct. 29, 2020

Related U.S. Application Data

(63) Continuation of application No. PCT/JP2019/000346, filed on Jan. 9, 2019.

(30) Foreign Application Priority Data

Jan. 12, 2018   (JP) ................................. 2018-003483

(51) Int. Cl.
*A61B 5/0235*     (2006.01)
*A61B 5/00*       (2006.01)
(Continued)

(52) U.S. Cl.
CPC ........ *A61B 5/0235* (2013.01); *A61B 5/02233* (2013.01); *A61B 5/681* (2013.01); *A61B 5/6832* (2013.01); *A61B 2562/0247* (2013.01)

(58) Field of Classification Search
CPC ... A61B 5/0235; A61B 5/02233; A61B 5/681; A61B 5/6832; A61B 2562/0247; A61B 5/02438; A61B 5/02225
See application file for complete search history.

(56) References Cited

U.S. PATENT DOCUMENTS

| 2011/0125037 A1* | 5/2011 | Iijima .................... A61B 5/681 600/500 |
| 2017/0127956 A1* | 5/2017 | Hirata ..................... F16K 31/02 |
| 2018/0119694 A1* | 5/2018 | Hashimoto ........... F04B 45/043 |

FOREIGN PATENT DOCUMENTS

| JP | H11-197122 A | 7/1999 |
| JP | 2013-220187 A | 10/2013 |

(Continued)

OTHER PUBLICATIONS

Google Patents machine translation of Applicant-disclosed JP2013220187A (Year: 2013).*

(Continued)

*Primary Examiner* — Alex M Valvis
*Assistant Examiner* — Justin Xu
(74) *Attorney, Agent, or Firm* — Oliff PLC

(57) ABSTRACT

A blood pressure measurement device includes an outer case; a base; a pump provided on the base such that the pump is shifted from a center of the outer case and located on one side as viewed in a circumferential direction of a living body; a drive unit provided on the base and located on one side of the pump as viewed in a direction orthogonal to the circumferential direction; an on-off valve provided on another side of the pump as viewed in the direction orthogonal to the circumferential direction; a pressure sensor provided on said another side of the pump as viewed in the direction orthogonal to the circumferential direction; and packing provided between the on-off valve and the pressure sensor and the base.

8 Claims, 19 Drawing Sheets

(51) Int. Cl.
*A61B 5/022* (2006.01)
*A61B 5/024* (2006.01)

(56) References Cited

FOREIGN PATENT DOCUMENTS

| JP | 6172351 B1 * | 8/2017 | ............ A61B 5/022 |
|----|---|---|---|
| WO | H06-114015 A | 4/1994 | |
| WO | 2013/157392 A1 | 10/2013 | |
| WO | 2017/203957 A1 | 11/2017 | |
| WO | 2018/008286 A1 | 1/2018 | |

OTHER PUBLICATIONS

Google Patents machine translation of JP6172351B1 (Year: 2017).*
Mar. 19, 2019 Search Report issued in International Patent Application No. PCT/JP2019/000346.

* cited by examiner

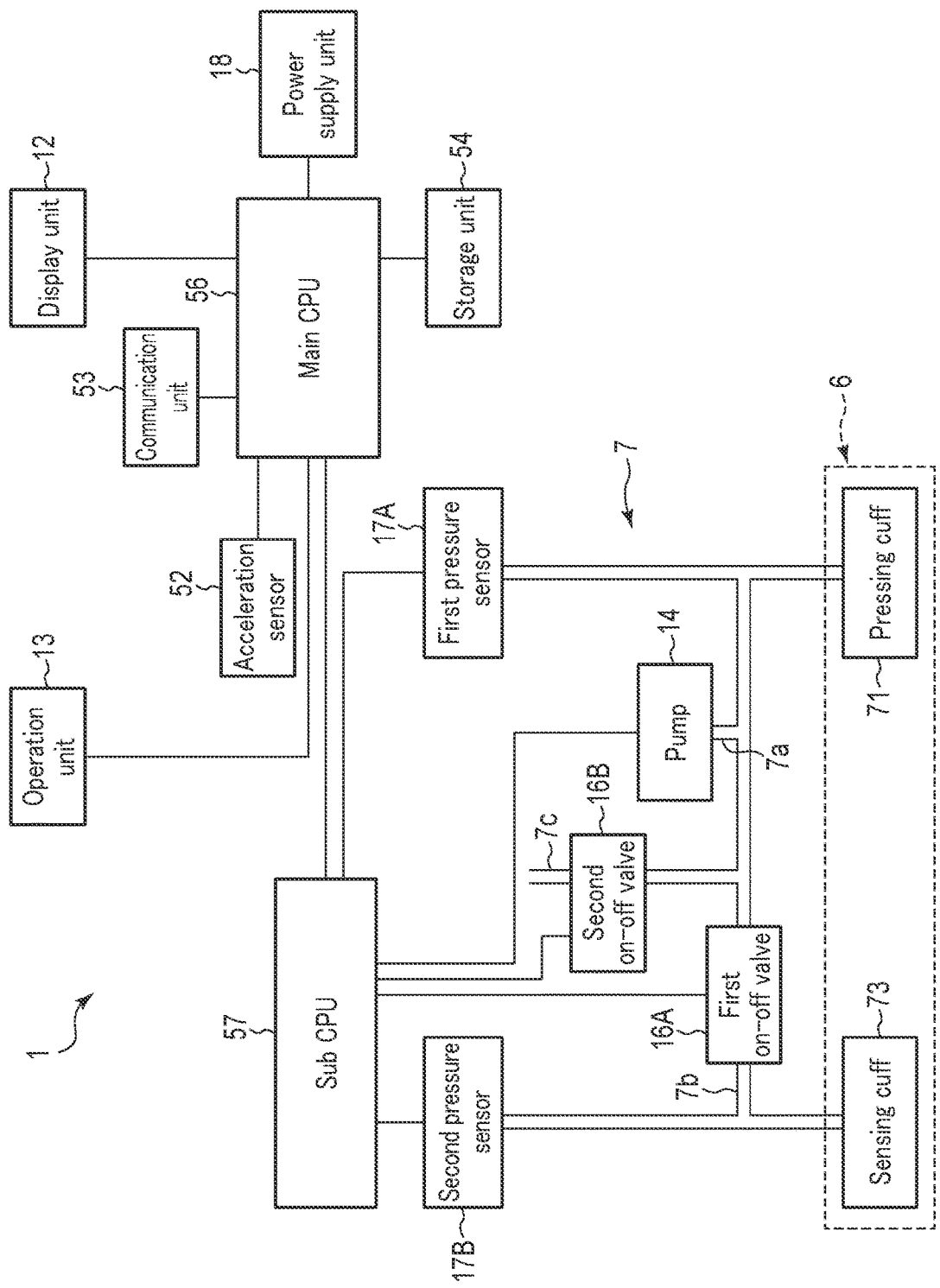
F I G. 4

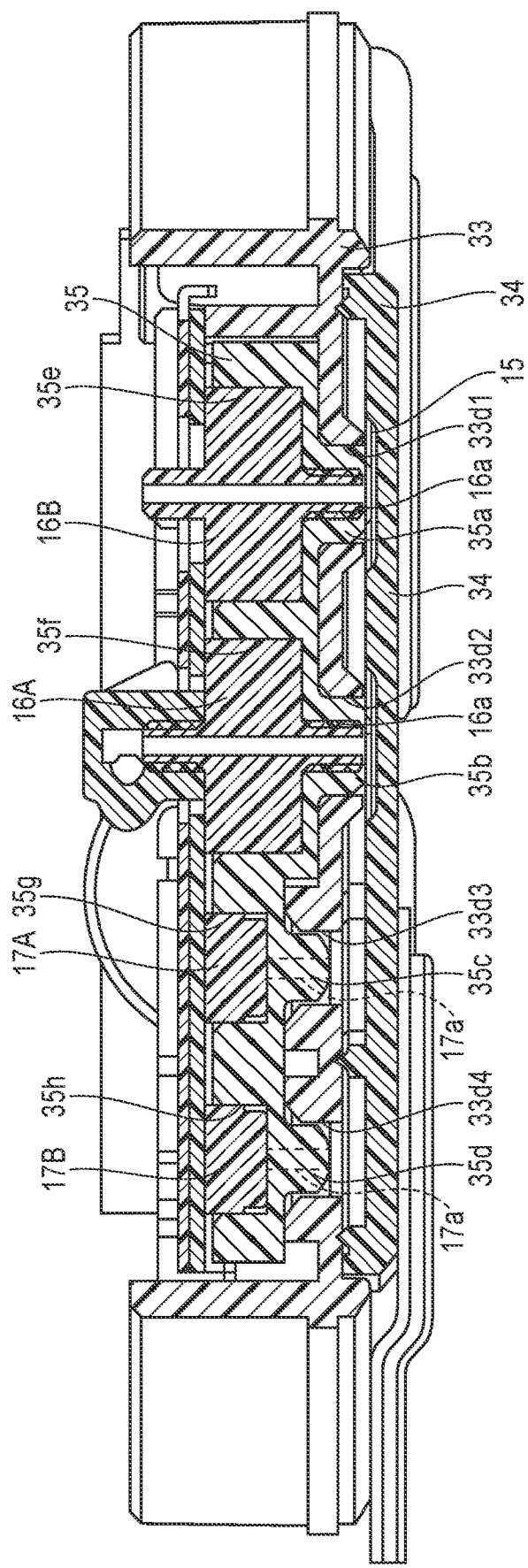
F I G. 8

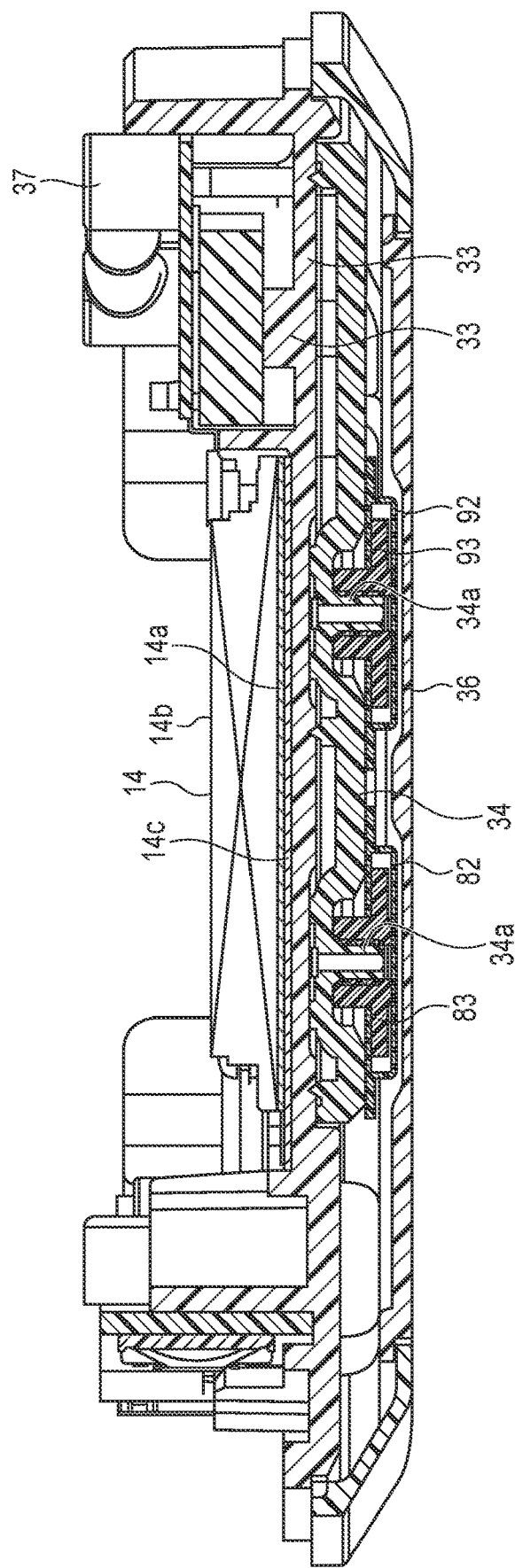
F I G. 9

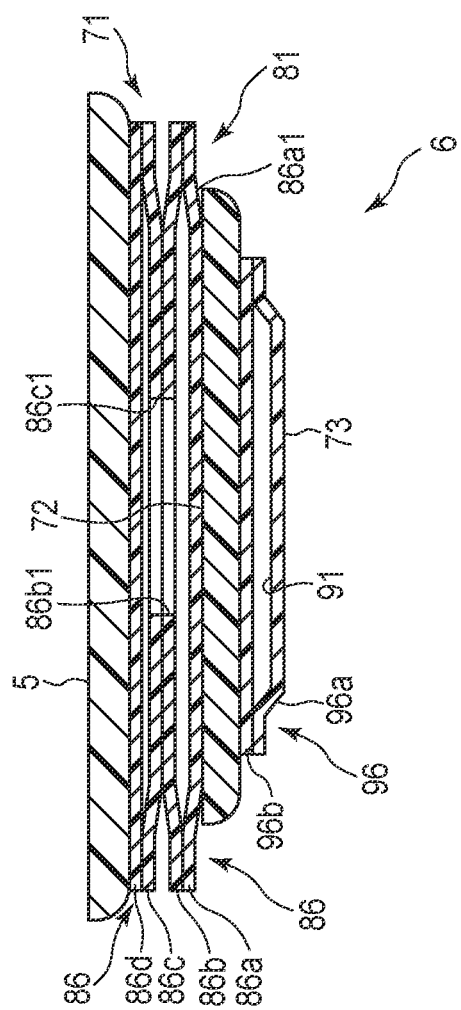
F I G. 13

BLOOD PRESSURE MEASUREMENT DEVICE

CROSS-REFERENCE TO RELATED APPLICATIONS

This is a Continuation Application of PCT application No. PCT/JP2019/000346, filed Jan. 9, 2019, which was published under PCT Article 21(2) in Japanese.

This application is based upon and claims the benefit of priority from Japanese Patent Application No. 2018-003483, filed Jan. 12, 2018, the entire contents of which are incorporated herein by reference.

BACKGROUND

Field

The present invention relates to a blood pressure measurement device that measures blood pressure.

Description of the Related Art

In recent years, blood pressure measurement devices used for measuring blood pressure are used not only in medical facilities but also at home as a means for confirming a health condition. A blood pressure measurement device measures blood pressure by detecting the vibration of the arterial wall, for example, by wrapping a cuff around the upper arm or wrist of a living body, inflating and contracting the cuff, and detecting the pressure of the cuff with a pressure sensor (see, for example, Jpn. Pat. Appln. KOKAI Publication No. 2013-220187).

It is required that a blood pressure measurement device used at home be reduced in size.

SUMMARY

In general, a blood pressure measurement device used at home includes a vibration motor that generates vibration for notifying the user of the start of measurement, and an operation unit operated by the user. The operation unit has buttons pressed by the user and sensors that detect an operation of the buttons. The vibration motor and the sensors are fixed to the base inside the case.

Where the blood pressure measurement device is reduced in size, a flow path portion through which air flows is inevitably near the vibration motor and the operation unit. If the distance by which the flow path portion is away from the vibration motor and the operation unit is short, the vibration generated by the vibration motor and the strain of the base caused by the operation of the operation unit adversely affect the flow path portion.

According to one aspect of the invention, a blood pressure measurement device can be provided, which includes an outer case; a base housed in the outer case; a pump provided on the base such that the pump is shifted from a center of the outer case and located on one side as viewed in a circumferential direction of a living body; a drive unit provided on the base such that the drive unit is located on one side of the pump as viewed in a direction orthogonal to the circumferential direction; an on-off valve provided on the base such that the on-off valve is located on another side of the pump as viewed in the direction orthogonal to the circumferential direction; a pressure sensor provided on the base such that the pressure sensor is located on said another side of the pump as viewed in the direction orthogonal to the circumferential direction; and packing provided between the on-off valve and the pressure sensor and the base.

It should be noted here that the fluid includes liquid and air. The fluid circuit is a circuit in which a fluid from the pump flows. The drive unit includes a vibration motor and a switch. The switch includes buttons operated by a user and sensors that detects an operation of the buttons.

According to this aspect, an on-off valve, a pressure sensor and packing are arranged on the opposite side of the drive unit as viewed in a direction orthogonal to the circumferential direction of the living body, with the pump located in between, so that the on-off valve, the pressure sensor, and the packing can be located away from the drive unit. It is therefore possible to reduce the adverse effects of the vibration generated by the driving unit and the strain of the base. In addition, the on-off valve and the pressure sensor are supported by the base with the packing interposed, so that the packing absorbs the vibration of the drive unit and the strain in the base.

In the aforementioned aspect of the invention, a blood pressure measurement device can be offered, in which the base includes a rib provided between the drive unit and the packing and extending in the direction orthogonal to the circumferential direction.

According to this aspect, the strength of the base can be improved by the rib.

In the aforementioned aspect of the invention, a blood pressure measurement device can be offered, in which the base includes a pump housing portion that houses the pump and that is partly constituted by the rib.

According to this aspect, the strength of the base can be improved by using the pump housing portion.

In the aforementioned aspect of the invention, a blood pressure measurement device can be offered, in which the pump is fixed to the base by means of a double-sided adhesive tape.

According to this aspect, the double-sided adhesive tape absorbs the vibration of the driving unit and the strain in the base.

In the aforementioned aspect of the invention, a blood pressure measurement device can be offered, in which the pump includes a pump base made of a metal plate, and a pump body.

According to this aspect, the strength of the base can be improved by the pump base portion.

The present invention can provide a blood pressure measurement device that can reduce the adverse effect of the vibration and the adverse effect of the strain generated in the base.

BRIEF DESCRIPTION OF THE DRAWINGS

FIG. 4 is a block diagram showing a configuration of the blood pressure measurement device.

FIG. 8 is a cross-sectional view showing a configuration of the device body of the blood pressure measurement device.

FIG. 9 is a cross-sectional view showing a configuration of the device body of the blood pressure measurement device.

FIG. 13 is a cross-sectional view showing a configuration of the curler and cuff structure body.

DETAILED DESCRIPTION

Hereinafter, an example of the blood pressure measurement device 1 according to one embodiment of the present invention will be described with reference to FIGS. 1 to 15.

Figure 1:
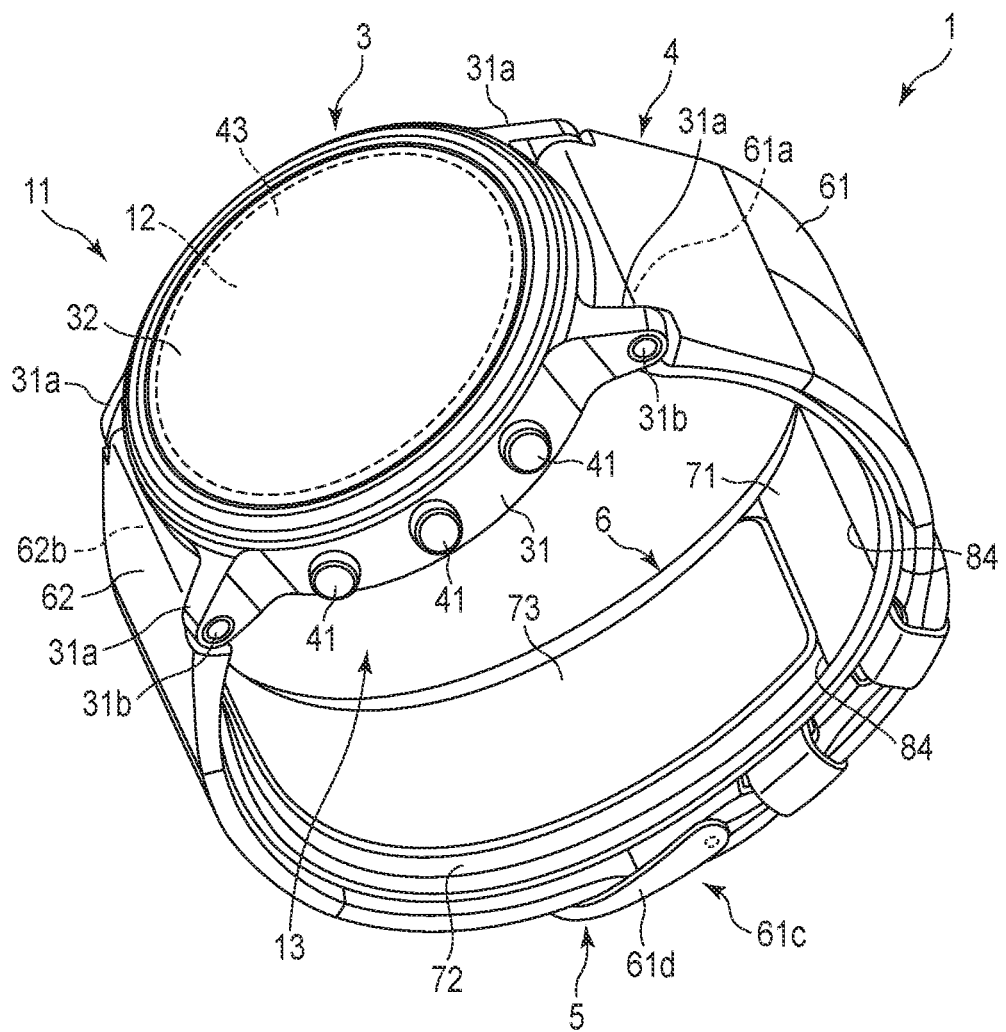
FIG. 1 is a perspective view showing a configuration of a blood pressure measurement device according to an embodiment of the present invention.
Figure 2:
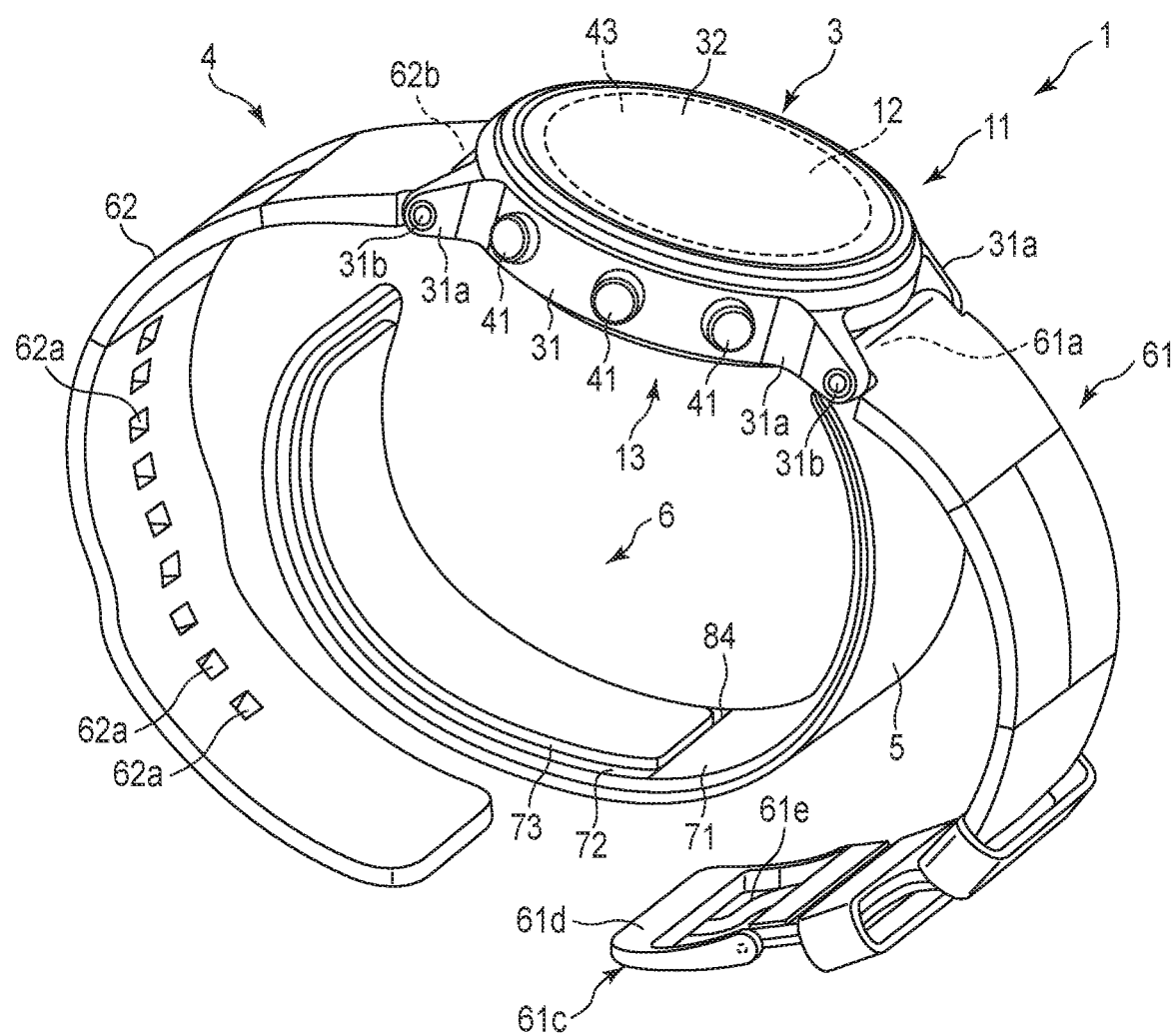
FIG. 2 is a perspective view showing a configuration of the blood pressure measurement device.
Figure 3:
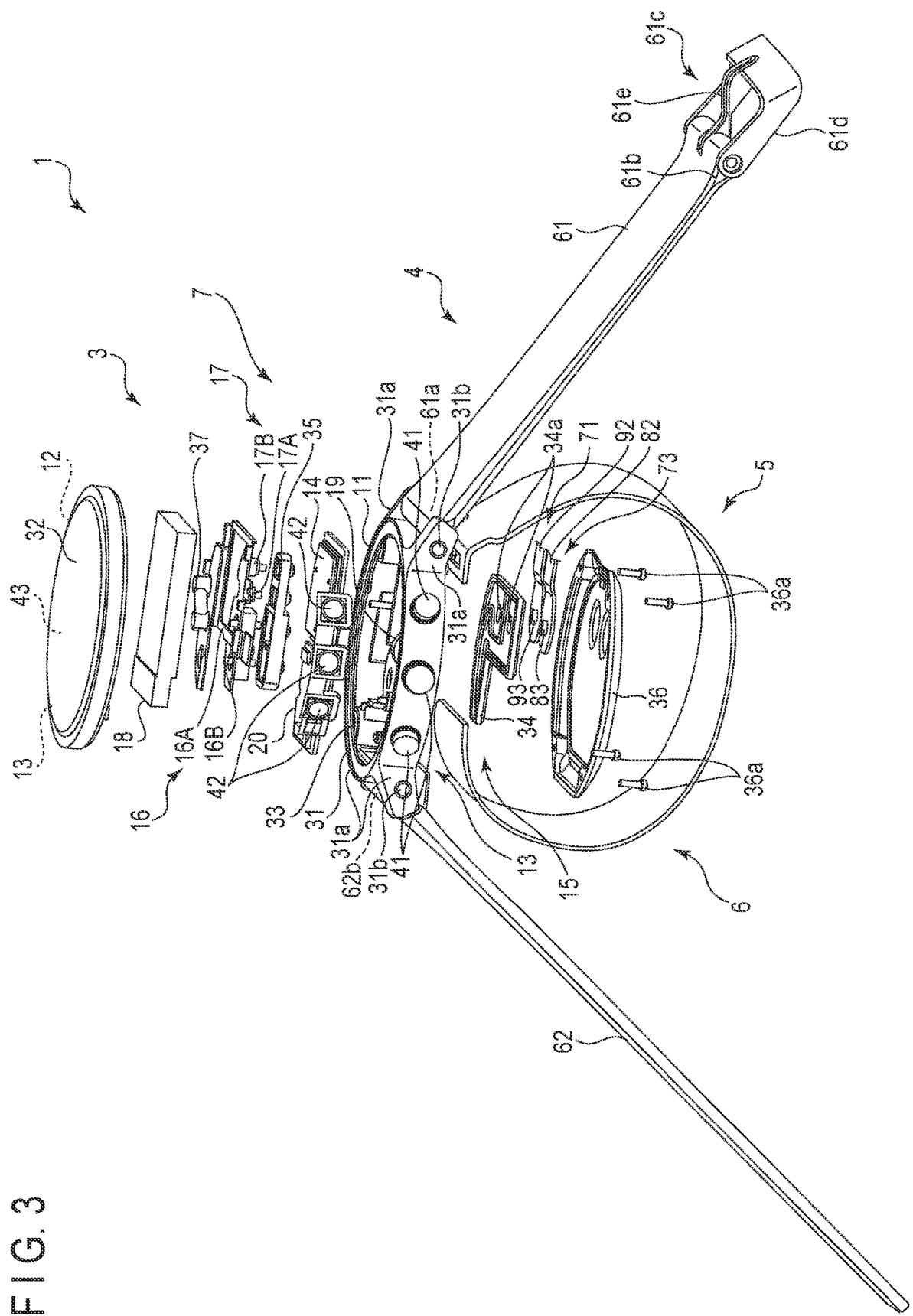
FIG. 3 is an exploded view showing a configuration of the blood pressure measurement device.
Figure 5:
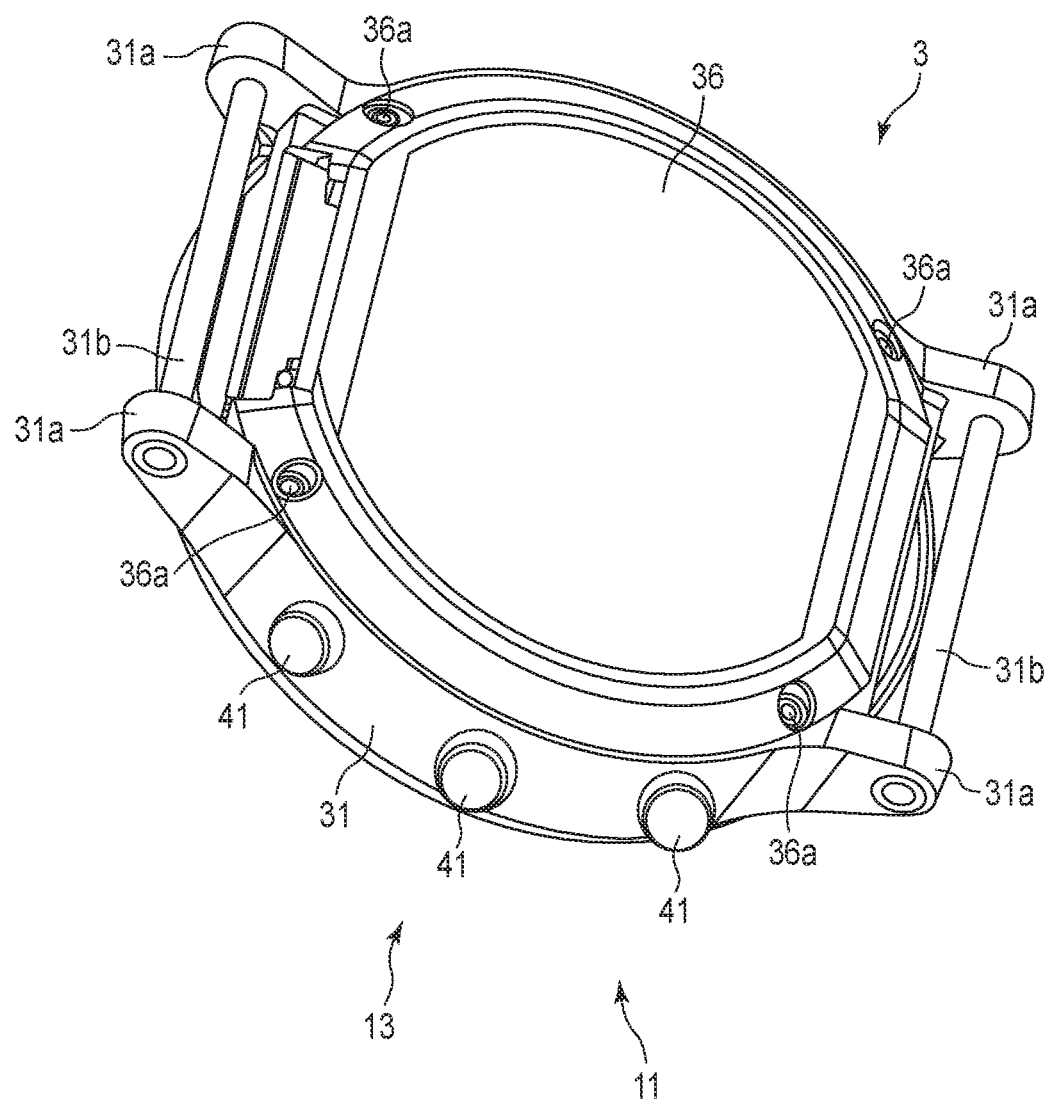
FIG. 5 is a perspective view showing a configuration of a device body of the blood pressure measurement device.
Figure 6:
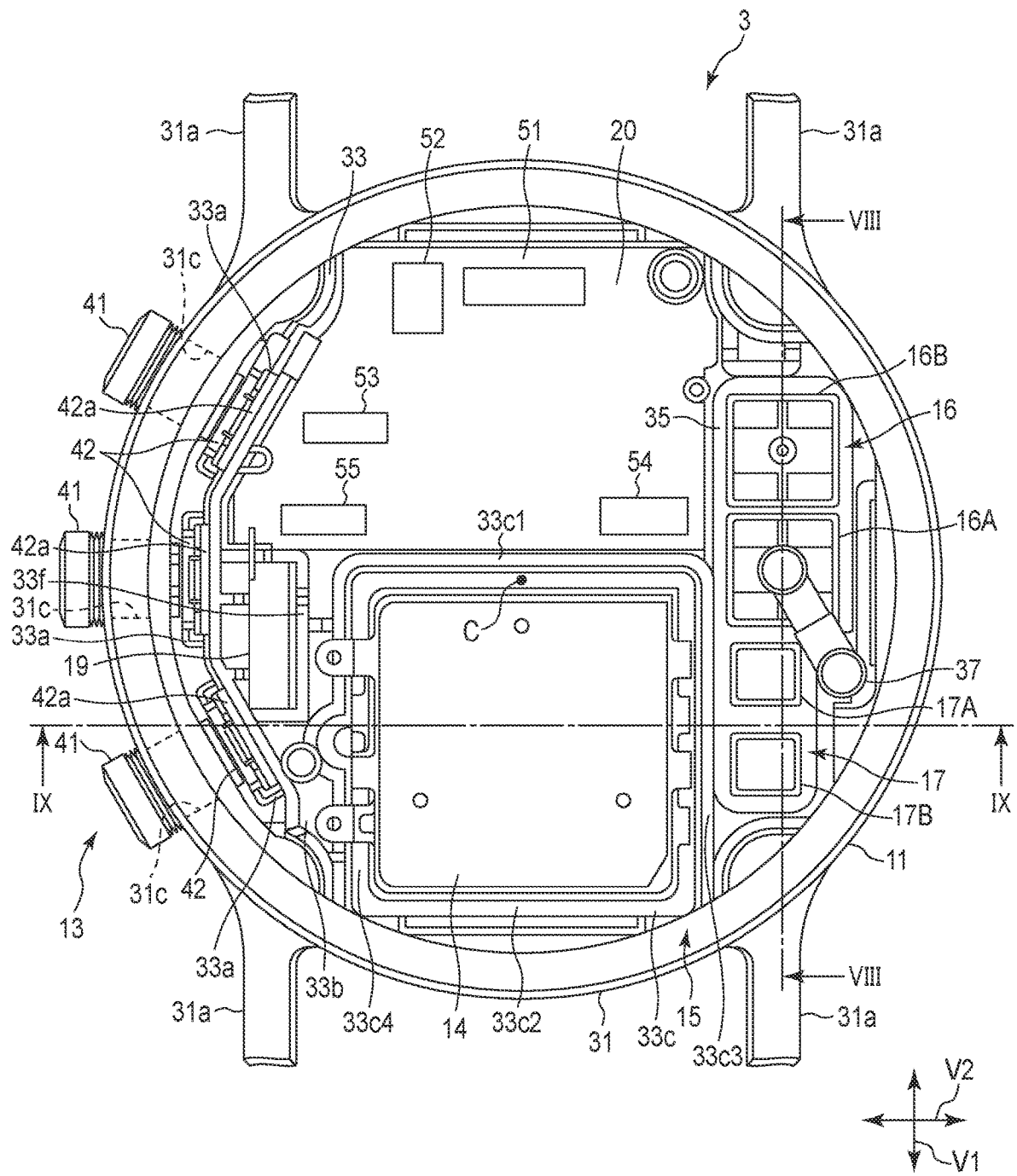
FIG. 6 is a plan view showing an internal configuration of the device body.
Figure 7:
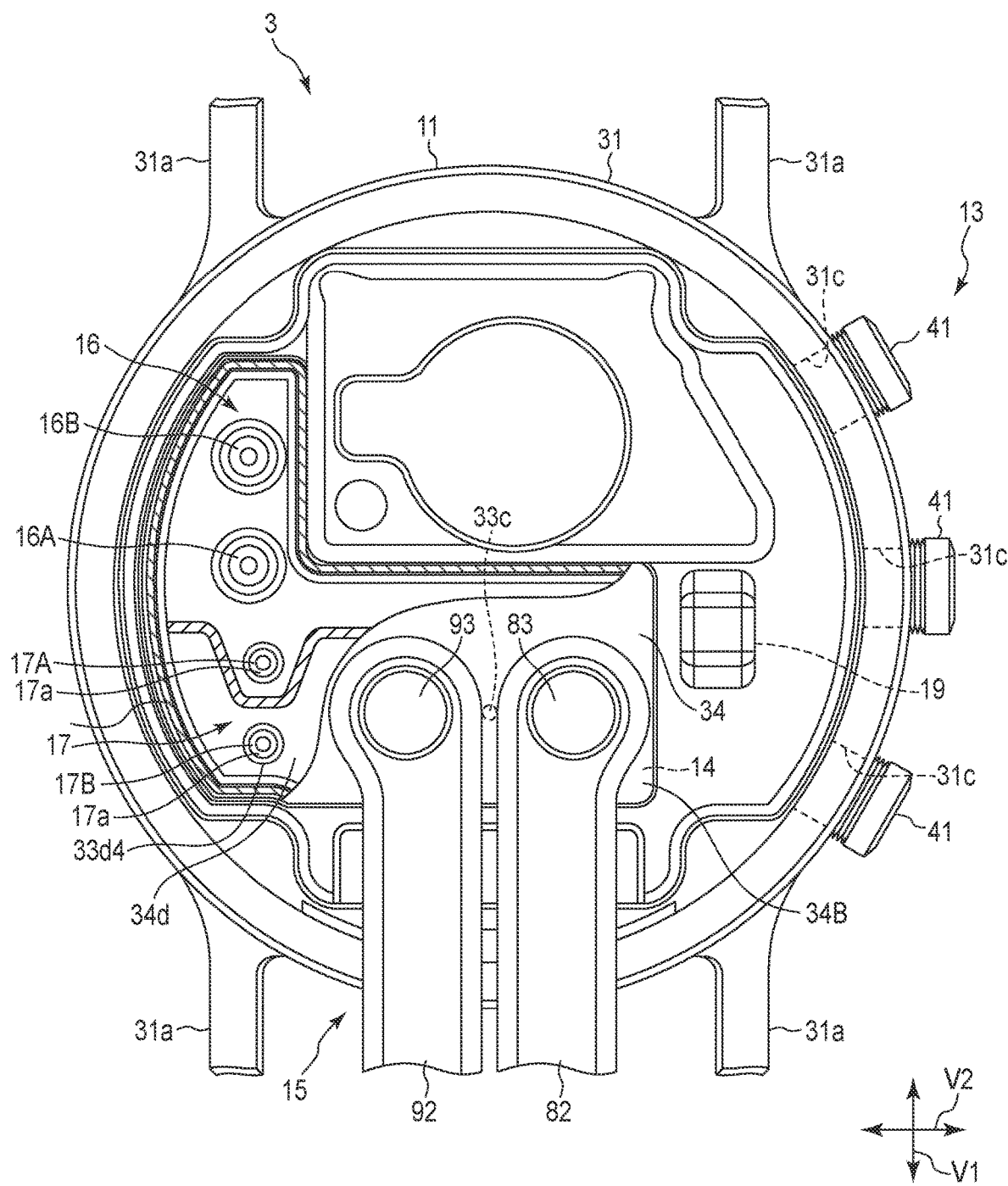
FIG. 7 is a plan view showing an internal configuration of the device body.

FIG. 1 is a perspective view showing how the blood pressure measurement device 1 according to one embodiment of the present invention looks like in a state where a strap 4 is closed. FIG. 2 is a perspective view showing how the blood pressure measurement device 1 looks like in a state where the strap 4 is open. FIG. 3 is an exploded view showing the configuration of the blood pressure measurement device 1. FIG. 4 is a block diagram showing the configuration of the blood pressure measurement device 1. FIG. 5 is a perspective view showing how the device body 3 of the blood pressure measurement device 1 looks like when viewed from the back cover 36 side. FIGS. 6 and 7 are plan views respectively showing how the internal structure of the device body 3 looks like when viewed from the windshield 32 side and the back cover 36 side.

Figure 10:
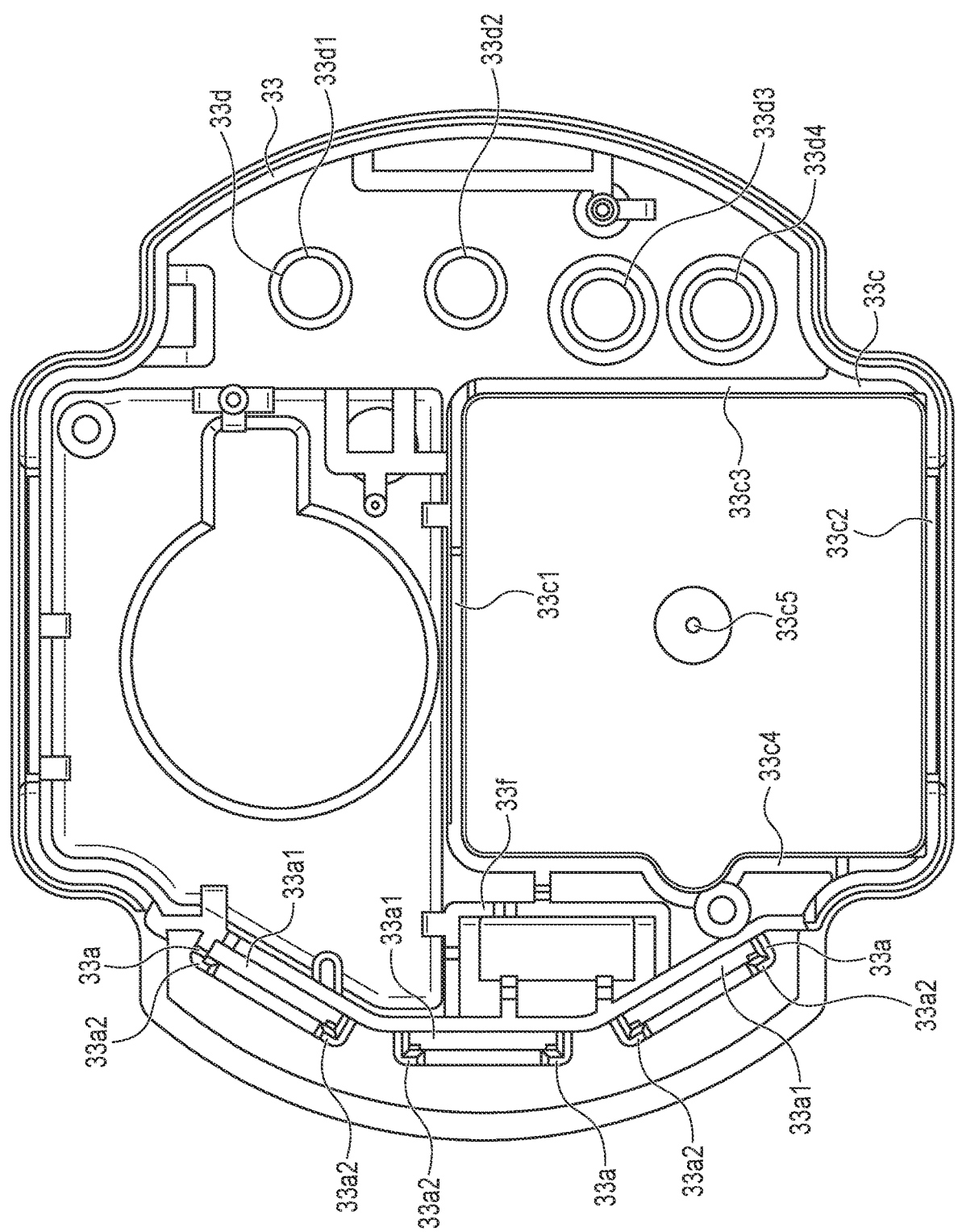
FIG. 10 is a plan view showing the base of the blood pressure measurement device.
Figure 11:
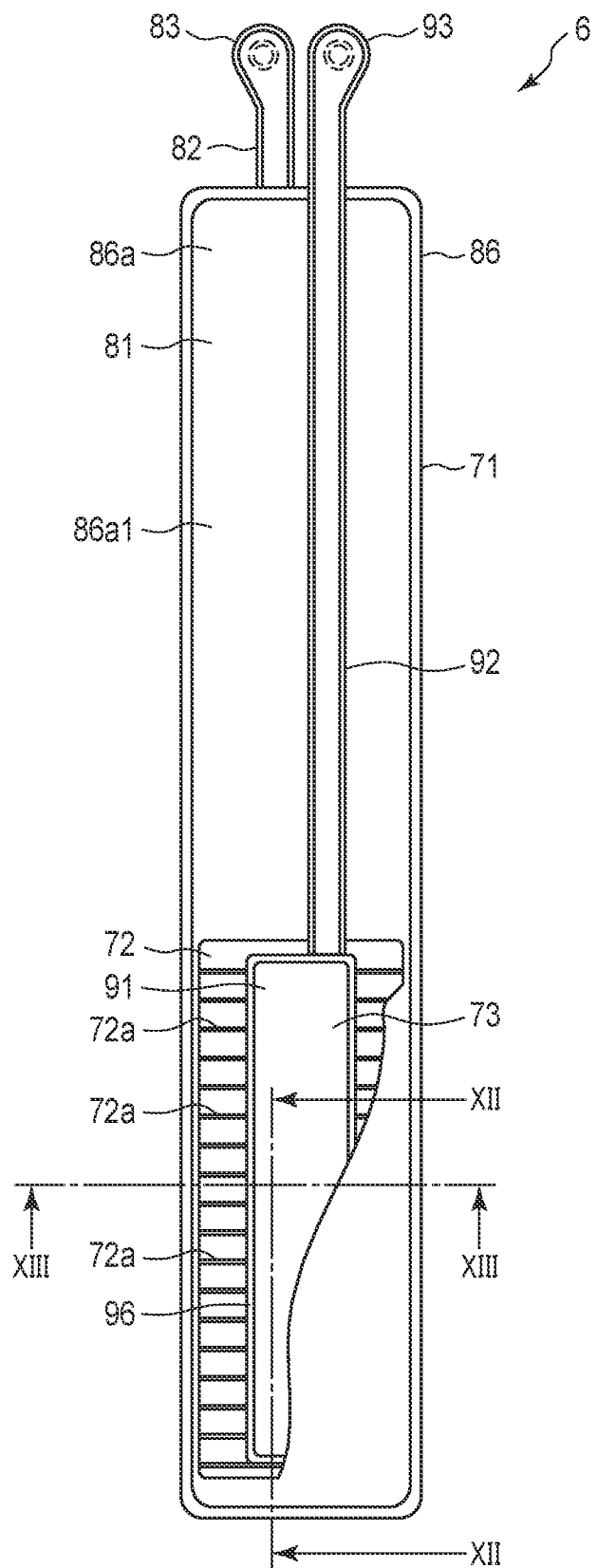
FIG. 11 is a plan view showing a configuration of a cuff structure of the blood pressure measurement device.

FIG. 8 is a cross-sectional view schematically showing the configuration of the device body 3 of the blood pressure measurement device 1 in a section taken along line XIII-XIII in FIG. 6. FIG. 9 is a cross-sectional view schematically showing the configuration of the device body 3 of the blood pressure measurement device 1 in a section taken along line IX-IX in FIG. 6. FIG. 10 is a plan view showing a configuration of a base 33 of the blood pressure measurement device 1. FIG. 11 is a plan view showing how the configuration of the cuff structure 6 of the blood pressure measurement device 1 is when viewed from the sensing cuff 73 side.

Figure 12:
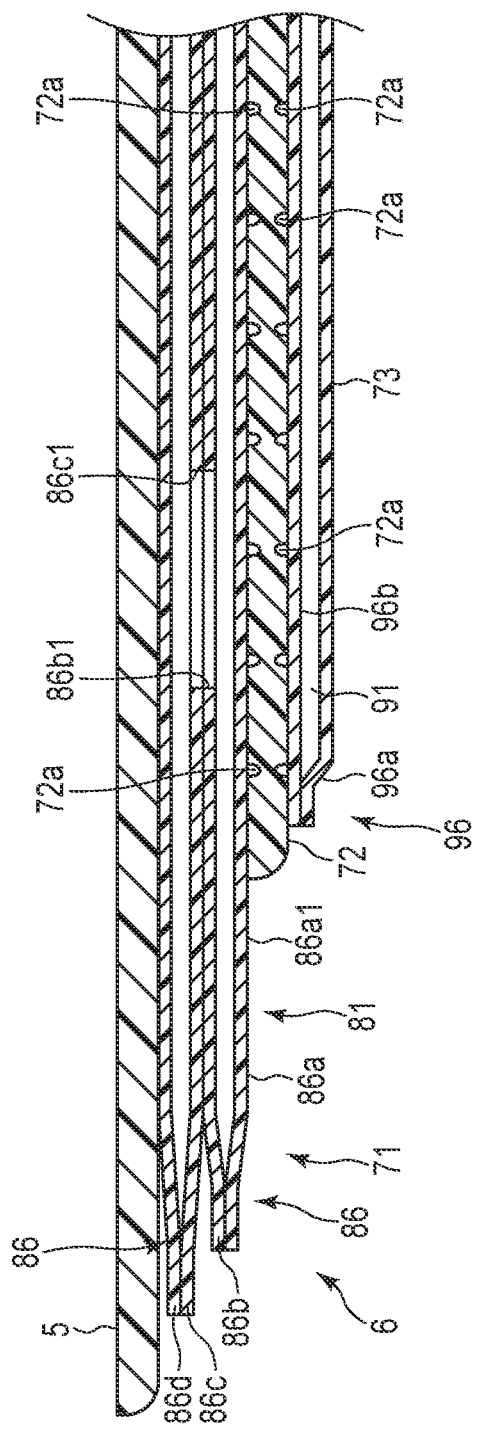
FIG. 12 is a cross-sectional view showing a configuration of a curler and a cuff structure both employed in the blood pressure measurement device.
Figure 14:
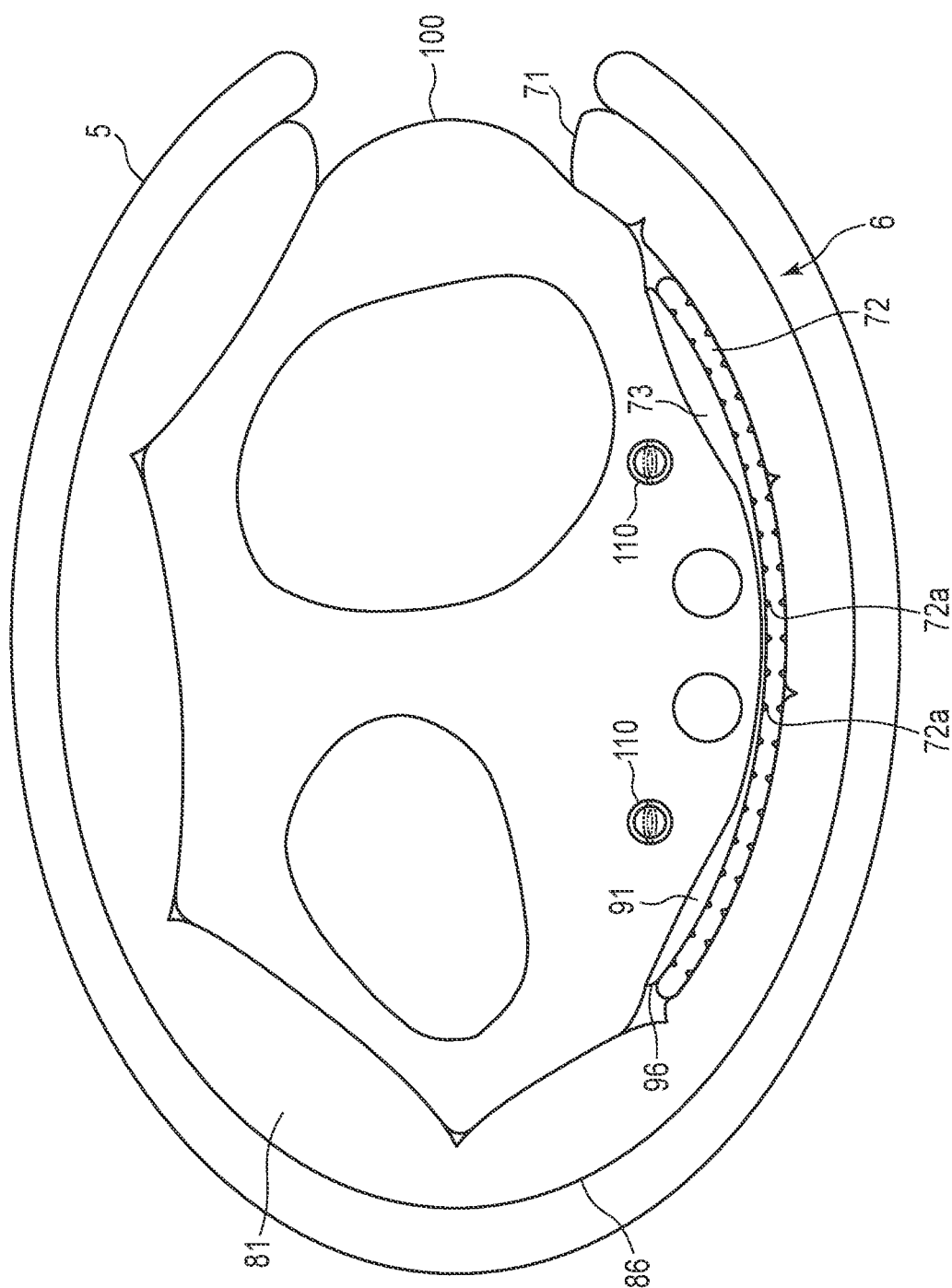
FIG. 14 is a side view schematically showing how a pressing cuff of the cuff structure is when it is inflated.
Figure 15:
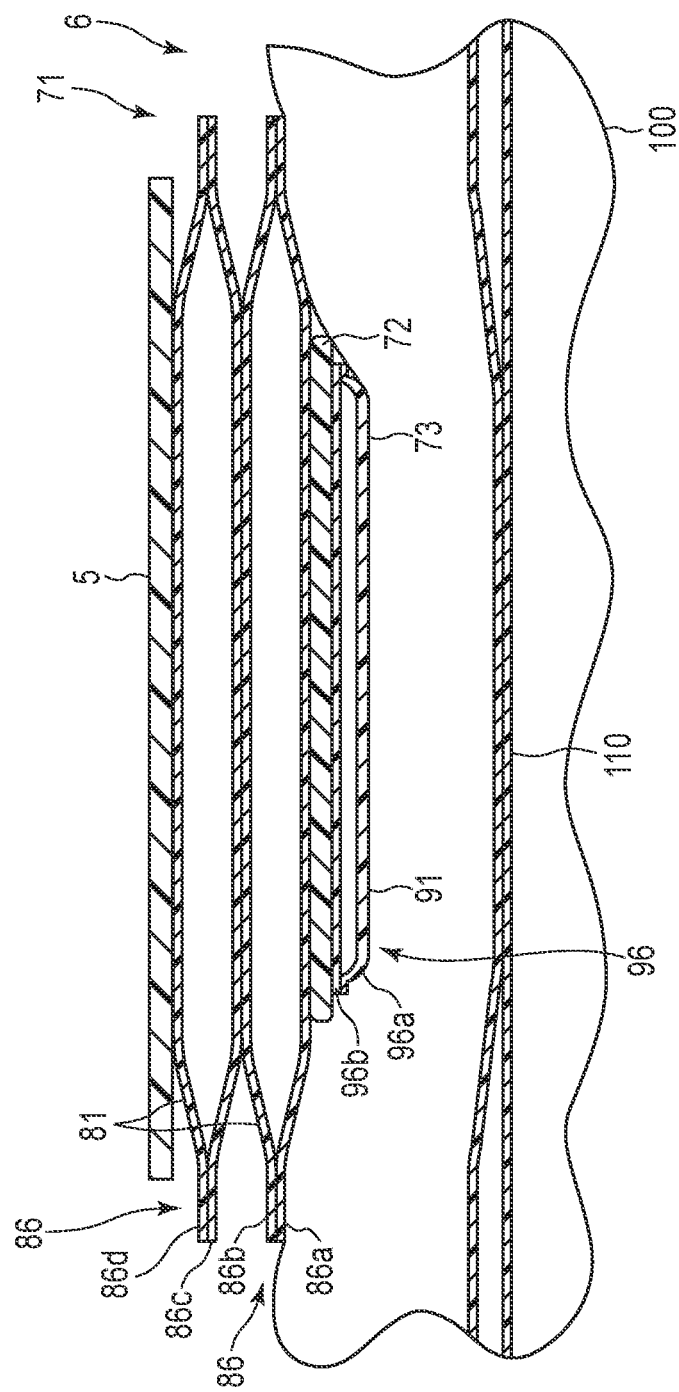
FIG. 15 is a cross-sectional view schematically showing how the pressing cuff of the cuff structure is when it is inflated.

FIG. 12 is a cross-sectional view schematically showing the configuration of the curler 5 and cuff structure 6 of the blood pressure measurement device 1 in a section taken along line XII-XII in FIG. 11. FIG. 13 is a cross-sectional view showing the configuration of the curler 5 and cuff structure 6 in a section taken along line XIII-XIII in FIG. 11. FIGS. 14 and 15 are respectively a side view and a cross-sectional view schematically showing an example in which the pressing cuff 71 and sensing cuff 73 of the cuff structure 6 are inflated. In FIG. 12, the curler 5 and the cuff structure 6 schematically shown as being linear for convenience of illustration, but actually they are curved in the configuration of the blood pressure measurement device 1.

The blood pressure measurement device 1 is an electronic blood pressure measurement device worn on a living body. The present embodiment will be described, referring to an electronic blood pressure measurement device embodied as a wearable device worn on the wrist 100 of the living body. As shown in FIGS. 1 to 15, the blood pressure measurement device 1 comprises a device body 3, a strap 4, a curler 5, a cuff structure 6 including both a pressing cuff 71 and a sensing cuff 73, and a fluid circuit 7.

As shown in FIGS. 1 to 10, the device body 3 comprises a case 11, a display unit 12, an operation unit 13, a pump 14, a flow path portion 15, an on-off valve 16, a pressure sensor 17, a power supply unit 18, a vibration motor 19, and a control board 20. The device body 3 is a supply device that supplies a fluid to the pressing cuff 71 by means of the pump 14, the on-off valve 16, the pressure sensor 17, the control board 20, etc.

The case 11 comprises an outer case 31, a windshield 32 that covers an upper opening of the outer case 31, a base 33 that is provided in the lower region of the inside of the outer case 31, a flow path cover 34 that covers part of the back surface of the base 33, packing 35 provided on part of the surface of the base 33, and a back cover 36 that covers the lower portion of the outer case 31. Also, the case 11 comprises a flow path tube 37 that constitutes part of the fluid circuit 7.

The outer case 31 is formed to have a cylindrical shape. The outer case 31 includes two pairs of lugs 31a provided at the positions symmetrical in the circumferential direction of the outer peripheral surface, and spring rods 31b respectively provided between the two pairs of lugs 31a. The windshield 32 is a circular glass plate.

As shown in FIGS. 6 and 7, the outer case 31 has holes 31c which are located between two pairs of lugs 31a and in which parts of the buttons 41 used for the operation unit 13 are arranged. In the present embodiment, three buttons 41 are used, so that three holes 31c are formed. The three holes 31c are arranged side by side in the circumferential direction of the outer case 31.

The base 33 holds the display unit 12, the operation unit 13, the pump 14, the on-off valve 16, the pressure sensor 17, the power supply unit 18, the vibration motor 19, and the control board 20. In addition, the base 33 constitutes part of the flow path portion 15. The on-off valve 16 and the pressure sensor 17 are supported by the base 33, with the packing 35 interposed.

The pump 14 is arranged at a position shifted from the center C of the outer case 31 as viewed in one of the circumferential directions of the living body, when the blood pressure measurement device 1 is attached to the living body. A specific example of the living body is the wrist 100 of the user. A specific example of the one direction of the circumferential directions of the living body when the blood pressure measurement device 1 is attached to the living body is a direction from the two lugs 31a on one side to the two lugs 31a on the other side. In the present embodiment, the circumferential directions of the living body when the blood pressure measurement device 1 is attached to the living body are defined as circumferential directions V1. The shift from the center C of the outer case 31 means that the center of the pump 14 and the center of the outer case 31 are shifted from each other.

The operation unit 13 is provided on the edge side of the base 33 and shifted from the pump 14 in one of the directions orthogonal to the circumferential directions V1. The on-off valve 16 and the pressure sensor 17 are provided on the edge side of the base 33 and shifted from the pump 14 in the other direction of the directions orthogonal to the circumferential directions V1. In the present embodiment, the directions orthogonal to circumferential directions V1 will be referred to as orthogonal directions V2.

As shown in FIGS. 6 and 10, sensor support portions 33*a* for holding the sensors 42 used in the operation unit 13 are formed at positions respectively opposed to the holes 31*c* in the vicinity of the periphery of the base 33. The sensor support portions 33*a* support the sensors 42 in a direction from the display unit 12 toward the back cover 36 and in an inward direction in the radial direction of the outer case 31.

A pump housing portion 33*c* that holds the pump 14 is formed on a surface 33*b* that is a display unit 12 side outer surface of the base 33. The pump housing portion 33*c* is arranged at a position shifted from the center C of the outer case 31 in one direction of the circumferential directions V1. In a specific example, the pump housing portion 33*c* is formed at a position shifted toward one pair of lugs 31*a*. It should be noted here that being shifted from the center C of the outer case 31 in one direction of the circumferential directions V1 means that the center of the pump housing portion 33*c* is shifted from the center C of the outer case 31 in one direction of the circumferential directions.

The pump housing portion 33*c* is made of ribs formed on the surface 33*b*. The pump housing portion 33*c* is formed such that the pump 14 can be fitted therein. In a specific example, the pump housing portion 33*c* is formed as a frame into which the pump base portion 14*a* of the pump 14 can be fitted. In a specific example, the pump base portion 14*a* has a rectangular flat plate shape, so that the pump housing portion 33*c* is formed as a rectangular frame into which the pump base portion 14*a* is fitted. The pump housing portion 33*c* includes a first rib 33*c*1 and a second rib 33*c*2 extending in the orthogonal direction V2, and a third rib 33*c*3 and a fourth rib 33*c*4 extending in the circumferential direction V1.

The base 33 has a hole 33*c*5 inside the pump housing portion 33*c*. The hole 33*c*5 extends through the base 33 and constitutes part of the flow path portion 15.

An attachment portion 33*d* for holding the packing 35, the on-off valve 16 and the pressure sensor 17 is formed on that edge side of the base 33 opposite to the edge side on which the sensor support portion 33*a* is formed, such that the pump housing portion 33*c* is sandwiched in the orthogonal direction V2. As shown in FIGS. 8 and 10, a specific example of the attachment portion 33*d* includes a first hole 33*d*1 into which the first nozzle 35*a* of the packing 35 is fitted, a second hole 33*d*2 into which the second nozzle 35*b* of the packing 35 is fitted, a third hole 33*d*3 into which the third nozzle 35*c* of the packing 35 is fitted, and a fourth hole 33*d*4 into which the fourth nozzle 35*d* of the packing 35 is fitted. In a specific example, the on-off valve 16 and the pressure sensor 17 are attached to the attachment portion 33*d*, with the packing 35 interposed.

The first hole 33*d*1, the second hole 33*d*2, the third hole 33*d*3, and the fourth hole 33*d*4 extend through the base 33 and communicate with the flow path portion 15. The first hole 33*d*1, the second hole 33*d*2, the third hole 33*d*3 and the fourth hole 33*d*4 are arranged side by side in the circumferential direction V1.

Portions of the attachment portion 33*d* configured in this manner, specifically, the second hole 33*d*2, the third hole 33*d*3 and the fourth hole 33*d*4, are arranged side by side in the orthogonal direction V2 in the pump housing portion 33*c*.

A motor support portion 33*f* that holds the vibration motor 19 is formed between the pump housing portion 33*c* and that edge of the surface 33*b* of the base 33 on which the sensor support portions 33*a* is formed. In a specific example, the motor support portion 33*f* is formed between the sensor support portion 33*a* and the pump housing portion 33*c*. The motor support portion 33*f* is formed as a frame slightly smaller than the vibration motor 19. The vibration motor 19 is forcibly inserted into the motor support portion 33*f*.

The flow path cover 34 is fixed to the back surface of the base 33, i.e., to the back cover 36 side outer surface of the base 33. The base 33 and the flow path cover 34 form part of the flow path portion 15 by providing a groove in one or both of them. The flow path cover 34 covers the hole 33*c*5, the first hole 33*d*1, the second hole 33*d*2, the third hole 33*d*3 and the fourth hole 33*d*4.

As shown in FIGS. 3 and 8, the packing 35 is fixed to the attachment portion 33*d*. In a specific example, the packing 35 is fixed to the attachment portion 33*d* by fitting the first nozzle 35*a*, the second nozzle 35*b*, the third nozzle 35*c* and the fourth nozzle 35*d* of the packing 35 into the first hole 33*d*1, the second hole 33*d*2, the third hole of and the fourth hole 33*d*4 of the base 33.

In a specific example, the first nozzle 35*a* is fitted into the first hole 33*d*1. The first nozzle 35*a* provides a seal between the peripheral surface of the first hole 33*d*1 and the nozzle 16*a* of the on-off valve 16. The second nozzle 35*b* is fitted into the second hole 33*d*2. The second nozzle 35*b* provides a seal between the peripheral surface of the second hole 33*d*2 and the nozzle 16*a* of the on-off valve 16. The third nozzle 35*c* is fitted into the third hole 33*d*3. The third nozzle 35*c* provides a seal between the peripheral surface of the third hole 33*d*3 and the nozzle 17*a* of the pressure sensor 17. The fourth nozzle 35*d* is fitted into the fourth hole 33*d*4. The fourth nozzle 35*d* provides a seal between the peripheral surface of the fourth hole 33*d*4 and the nozzle 17*a* of the pressure sensor 17.

The packing 35 is formed of an elastic body. The elastic body mentioned here refers to a body that is capable of absorbing the vibration generated by the vibration motor 19 and the strain in the base 33 caused by the operation of the buttons 41 of the operation unit 13, and that can provide a seal between the base 33 on one hand and the on-off valve 16 and the pressure sensor 17 on the other hand.

The packing 35 is formed to have a rectangular parallelepiped shape in which a plurality of recesses for housing the on-off valves 16 and the pressure sensors 17 are formed. In the present embodiment, two on-off valves 16 are used and two pressure sensors 17 are used, so that a specific example of the packing 35 includes a first recess 35*e*, a second recess 35*f*, a third recess 35*g* and a fourth recess 35*h*.

The first recess 35*e* houses one of the on-off valves 16. Since the on-off valves 16 of the present embodiment have, for example, a rectangular parallelepiped shape, rectangular recesses are formed in a specific example. The second recess 35*f* houses the other one of the on-off valves 16. In a specific example, the second recess 35*f* is formed as a rectangular recess. The third recess 35*g* houses one of pressure sensors 17. Since the pressure sensors 17 of the present embodiment have, for example, a rectangular parallelepiped shape, rectangular recesses are formed in a specific example. The fourth recess 35h houses the other one of the pressure sensors 17. In a specific example, the fourth recess 35h is formed as a rectangular recess. The first recess 35e, the second recess 35f, the third recess 35g and the fourth recess 35h are arranged in the circumferential direction V1.

The inner surface of the first recess 35e provides a seal between itself and the on-off valve 16. A first nozzle 35a is formed on the back surface of the first recess 35e, i.e., on the outer surface on the front surface 33b side of the base 33. The first nozzle 35a communicates with the inside of the first recess 35e. The nozzle 16a of the on-off valve 16 is fitted into the first nozzle 35a.

The inner surface of the second recess 35f provides a seal between itself and the on-off valve 16. A second nozzle 35b is formed on the back surface of the second recess 35f, i.e., on the outer surface on the front surface 33b side. The second nozzle 35b communicates with the inside of the second recess 35f. The nozzle 16a of the on-off valve 16 is fitted into the second nozzle 35b.

The inner surface of the third recess 35g provides a seal between itself and the pressure sensor 17. A third nozzle 35c is formed on the back surface of the third recess 35g, i.e., on the outer surface on the front surface 33b side. The third nozzle 35c communicates with the inside of the third recess 35g. The nozzle 17a of the pressure sensor 17 is fitted into the third nozzle 35c.

The inner surface of the fourth recess 35h provides a seal between itself and the pressure sensor 17. A fourth nozzle 35d is formed on the back surface of the fourth recess 35h, i.e., on the outer surface on the front surface 33b side. The fourth nozzle 35d communicates with the inside of the fourth recess 35h. The nozzle 17a of the pressure sensor 17 is fitted into the fourth nozzle 35d.

The back cover 36 covers the living body side end of the outer case 31. The back cover 36 is fixed to the outer case 31 or to the living body side end of the base 33 with, for example, four screws 36a.

The flow path tube 37 constitutes part of the flow path portion 15. The flow path tube 37 connects, for example, the on-off valve 16 and part of the flow path portion 15 of the base 33.

The display unit 12 is arranged on the base 33 of the outer case 31 and directly below the windshield 32. The display unit 12 is electrically connected to the control board 20. The display unit 12 is, for example, a liquid crystal display or an organic electroluminescence display. The display unit 12 displays various information, including a date and time, blood pressure values such as systolic blood pressure and diastolic blood pressure, and measurement results such as a heart rate.

The operation unit 13 is configured to enable commands to be entered from a user. The operation unit 13 is an example of the drive unit of the present invention. For example, the operation unit 13 includes a plurality of buttons 41 provided on the case 11, a plurality of sensors 42 that detect an operation of the buttons 41, and a touch panel 43 provided on either the display unit 12 or the windshield 32. The operation unit 13 is operated by a user and converts a command into an electric signal. The sensor 42 and the touch panel 43 are electrically connected to the control board 20 and output an electric signal to the control board 20.

For example, three buttons 41 are provided. Parts of the buttons 41 are arranged in holes 31c formed in the outer case 31. Parts of the buttons 41 are projected from the outer peripheral surface of the outer case 31. Parts of the buttons 41 are connected to the sensors 42.

The plurality of sensors 42 are supported by the sensor support portions 33a formed on the base 33. In a specific example, the plurality of sensors 42 are formed such that they can be held on the base 33 in a vertical posture. The vertical posture mentioned here is a posture orthogonal to the direction in which the buttons 41 are pushed. The plurality of sensors 42 are supported in the direction from the display unit 12 toward the back cover 36 and in the pushing direction of the buttons 41. The touch panel 43 is provided, for example, integrally with the windshield 32.

The pump 14 is, for example, a piezoelectric pump. The pump 14 compresses air and supplies the compressed air from the hole 33c5 of the base 33 to the cuff structure 6 via the flow path portion 15. The pump 14 is electrically connected to the control unit 55. The pump 14 includes a plate-shaped pump base portion 14a formed of metal, specifically, stainless steel, and a pump body 14b provided on the pump base portion 14a.

The pump base portion 14a is formed, for example, in a rectangular shape having the same outer shape as the pump housing portion 33c. The pump base portion 14a has a hole through which the compressed air discharged from the pump body 14b passes. The pump base portion 14a is fitted in a frame-shaped pump housing portion 33c. The pump base portion 14a is fixed to surface 33b by means of the double-sided adhesive tape 14c.

The flow path portion 15 is an air flow path configured by a groove or the like provided in a flow path cover 34 that covers the major surface on the back cover 36 side of the base 33 and on the back cover 36 side of the base 33. The flow path portion 15 constitutes a flow path that connects the pump 14 to the pressing cuff 71 and a flow path that connects the pump 14 to the sensing cuff 73. In addition, the flow path portion 15 constitutes a flow path that connects the pressing cuff 71 to the atmosphere and a flow path that connects the sensing cuff 73 to the atmosphere.

The flow path cover 34 has a connected portion 34a to which the pressing cuff 71 and the sensing cuff 73 are connected. The connected portion 34a is, for example, a cylindrical nozzle provided in the flow path cover 34.

The on-off valve 16 opens or closes part of the flow path portion 15. For example, a plurality of on-off valves 16 are provided, and a combination of the open/closed states of the on-off valves 16 selectively opens or closes a flow path connecting the pump 14 to the pressing cuff 71, a flow path connecting the pump 14 to the sensing cuff 73, and a flow path connecting the pressing cuff 71 to the atmosphere and a flow path connecting the sensing cuff 73 to the atmosphere. For example, two on-off valves 16 are used.

One of the on-off valves 16 is formed, for example, in a rectangular parallelepiped shape having the same outer shape as the first recess 35e. The on-off valve 16 is fitted in the first recess 35e. The nozzle 16a of the on-off valve 16 is fitted in the first nozzle 35a. The nozzle 16a and the first nozzle 35a are sealed from each other. The opening at the tip of the nozzle 16a is arranged in the flow path portion 15.

The other on-off valve 16 is formed, for example, in a rectangular parallelepiped shape having the same outer shape as the second recess 35f. The other on-off valve 16 is fitted in the second recess 35f. The nozzle 16a of the other on-off valve 16 is fitted in the second nozzle 35b. The nozzle 16a and the second nozzle 35b are sealed from each other. The opening at the tip of the nozzle 16a is arranged in the flow path portion 15.

The pressure sensor 17 detects pressures of the pressing cuff 71 and the sensing cuff 73. The pressure sensor 17 is electrically connected to the control board 20. The pressure sensor 17 is electrically connected to the control board 20, converts detected pressure into an electric signal, and outputs the electric signal to the control board 20. The pressure sensor 17 is provided, for example, in a flow path connecting the pump 14 to the pressing cuff 71 and a flow path connecting the pump 14 to the sensing cuff 73. Since these flow paths are continuous with the pressing cuff 71 and the sensing cuff 73, the pressure in these flow paths is equal to the pressure in the internal spaces of the pressing cuff 71 and sensing cuff 73. As mentioned above, two pressure sensors 17 are used. A specific example of each the pressure sensor 17 is formed in a rectangular parallelepiped shape.

One of the pressure sensors 17 is formed, for example, in a rectangular parallelepiped shape having the same outer shape as the third recess 35g. One of the pressure sensors 17 is fitted in the third recess 35g. As shown in FIG. 8, the nozzle 17a of one of the pressure sensors 17 is fitted in the third nozzle 35c. The nozzle 17a and the third nozzle 35c are sealed from each other. The opening at the tip of the nozzle 17a is arranged in the flow path portion 15.

The other pressure sensors 17 is formed, for example, in a rectangular parallelepiped shape having the same outer shape as the fourth recess 35h. The other pressure sensors 17 is fitted in the fourth recess 35h. The nozzle 17a of the other pressure sensor 17 is fitted in the fourth nozzle 35d. The nozzle 17a and the fourth nozzle 35d are sealed from each other. The opening at the tip of the nozzle 17a is arranged in the flow path portion 15.

The power supply unit 18 is, for example, a secondary battery such as a lithium ion battery. The power supply unit 18 is electrically connected to the control board 20. The power supply unit 18 supplies power to the control board 20.

The vibration motor 19 is arranged in the motor support portion 33f as shown in FIG. 6. In a specific example, the vibration motor 19 is forcibly inserted and fitted into the motor support portion 33f. The vibration motor 19 is an example of the drive unit of the present invention.

As shown in FIGS. 4 and 6, the control board 20 comprises, for example, a board 51, an acceleration sensor 52, a communication unit 53, a storage unit 54, and a control unit 55. The control board 20 is configured by mounting the acceleration sensor 52, the communication unit 53, the storage unit 54, and the control unit 55 on the board 51.

The board 51 is arranged in the direction in which a pair of lugs 31a are arranged such that it is opposed to the pump 14, and is fixed to the base 33 with screws or the like.

The acceleration sensor 52 is, for example, a triaxial acceleration sensor. The acceleration sensor 52 outputs, to the control unit 55, an acceleration signal representing accelerations that are applied to the device body 3 in three directions orthogonal to each other. For example, the acceleration sensor 52 is used to measure the activity amount of the living body wearing the blood pressure measurement device 1 based on detected accelerations.

The communication unit 53 is configured to transmit/receive information to/from an external device wirelessly or by wire. The communication unit 53 transmits, for example, information controlled by the control unit 55 and information such as a measured blood pressure value and a pulse rate to an external device via a network. Also, the communication unit 53 receives a software update program or the like from the external device via the network and sends it to the control unit.

In the present embodiment, the network is, for example, the Internet, but the network is not limited to this, and may be a network such as a LAN (Local Area Network) in a hospital, or direct communications with an external device that are performed using a cable with a predetermined standard terminal such as USB. Therefore, the communication unit 53 may include a plurality of wireless antennas, micro USB connectors, etc.

The storage unit 54 stores in advance program data for controlling the entire blood pressure measurement device 1 and the fluid circuit 7, setting data for setting various functions of the blood pressure measurement device 1, calculation data for calculating a blood pressure value and a pulse based on the pressure measured by the pressure sensor 17, etc. Also, the storage unit 54 stores information such as a measured blood pressure value and a pulse.

The control unit 55 includes a single CPU or a plurality of CPUs, and controls the operation of the entire blood pressure measurement device 1 and the operation of the fluid circuit 7. The control unit 55 is electrically connected to the display unit 12, the operation unit 13, the pump 14, the on-off valves 16, the pressure sensors 17 and the vibration motor 19, and supplies electric power to them. Further, the control unit 55 controls the operations of the display unit 12, pump 14 and the on-off valves 16 based on electric signals output from the operation unit 13 and the pressure sensor 17. Further, the control unit 55 controls the operation of the vibration motor 19 based on electric signals output from the operation unit 13 and the pressure sensors 17.

For example, as shown in FIG. 4, the control unit 55 includes a main CPU 56 that controls the operation of the entire blood pressure measurement device 1, and also includes a sub CPU 57 that controls the operation of the fluid circuit 7. For example, when a command for measuring blood pressure is input from the operation unit 13, the sub CPU 57 drives the pump 14 and the on-off valves 16 and sends compressed air to the pressing cuff 71 and the sensing cuff 73. Further, for example, the sub CPU 57 drives the vibration motor 19 when a command for measuring blood pressure is input from the operation unit 13.

Also, the sub CPU 57 controls the driving and stopping of the pump 14 and the opening and closing of the on-off valves 16 based on electric signals output from the pressure sensor 17, such that compressed air is selectively supplied to the pressing cuff 71 and the sensing cuff 73 and such that the pressures of the pressing cuff 71 and the sensing cuff 73 are selectively decreased. The main CPU 56 obtains measurement results such as blood pressure values, e.g., systolic blood pressure and diastolic blood pressure, and a heart rate, based on electric signals output from the pressure sensor 17, and outputs an image signal corresponding to the measurement results to the display unit 12.

As shown in FIGS. 1 to 3, the strap 4 includes a first strap 61 provided for one pair of lugs 31a and the spring rod 31b, and a second strap 62 provided for the other pair of lugs 31a and the spring rod 31b.

The first strap 61 is referred to as a parent and is formed to have a band shape. The first strap 61 is includes a first hole portion 61a provided at one end portion and being orthogonal to the longitudinal direction of the first strap 61, a second hole portion 61b provided at the other end portion and being orthogonal to the longitudinal direction of the first strap 61, and a buckle 61c provided for the second hole portion 61b. The first hole portion 61a can receive the spring rod 31b inserted thereinto and has an inner diameter permitting the first strap 61 to rotate with respect to the spring rod 31b. That is, the first strap 61 is rotatably held by the outer case 31 between the pair of lugs 31a and with the spring rod 31b being within the first hole portion 61a.

The second hole portion 61b is provided at the tip end of the first strap 61.

The buckle 61c includes a rectangular frame-shaped body 61d and a stick 61e rotatably attached to the frame-shaped body 61d. One side of the frame-shaped body 61d, to which the stick 61e is attached, is inserted into the second hole portion 61b and is rotatably attached to the first strap 61.

The second strap 62 is referred to as a sword tip and is formed to have a strap shape with a width that enables insertion into the frame-shaped body 61d. The second strap 62 has a plurality of small holes 62a into which the stick 61e can be inserted. The second strap 62 has a third hole portion 62b provided at one end portion and being orthogonal to the longitudinal direction of the second strap 62. The third hole portion 62b can receive the spring rod 31b inserted thereinto and has an inner diameter permitting the second strap 62 to rotate with respect to the spring rod 31b. That is, the second strap 62 is rotatably held by the outer case 31 between the pair of lugs 31a and with the spring rod 31b being within the third hole portion 62b.

In the strap 4 mentioned above, the second strap 62 is inserted into the frame-shaped body 61d and the stick 61e is inserted into one small hole 62a, whereby the first strap 61 and the second strap 62 are integrally connected, and together with the outer case 31, form an annular shape conformable to the wrist 100 in the circumferential direction.

The curler 5 is made of a resin material and has a band shape that curves along the circumferential direction of the wrist. The curler 5 is configured, for example, such that one end is fixed between the base 33 of the device body 3 and the flow path cover 34 and the back cover 36, and such that the other end is arranged close to the device body 3.

As shown in FIGS. 1 to 3 and FIG. 14, the curler 5 is formed of a resin material having a shape that is curved along the circumferential direction V1 of the wrist 100 in a side view viewed in a direction orthogonal to the circumferential direction of the wrist, i.e., in the longitudinal direction of the wrist. The curler 5 extends from the device body such that it extends from the back of the wrist to the palm by way of one side and further to the central side on the other side. That is, the curler 5 is curved along the circumferential direction of the wrist so as to cover most of the circumferential direction of the wrist 100, and both ends of the curler 5 are separate by a predetermined distance.

The curler 5 has such hardness as provides both flexibility and shape retention. The flexibility mentioned here means that the shape of the curler 5 is deformed in the radial direction when an external force is applied thereto. For example, when the curler 5 is pressed by the strap 4, the curler 5 moves closer to the wrist, or the shape of the curler 5 becomes similar to that of the wrist or moves in conformity with the shape of the wrist in a side view. The shape retention means that the curler 5 can maintain a pre-fabricated shape when an external force is not applied, and in the present embodiment, the shape of the curler 5 can maintain a shape that curves along the circumferential direction of the wrist. The curler 5 is formed of a resin material. For example, the curler 5 is formed of polypropylene and has a thickness of approximately 1 mm. The curler 5 holds the cuff structure 6 along the inner surface shape of the curler 5.

As shown in FIGS. 1 to 4 and FIGS. 12 to 14, the cuff structure 6 comprises a pressing cuff 71, a back plate 72 and a sensing cuff 73. The cuff structure 6 is a structure formed by integrally stacking the pressing cuff 71, the back plate 72 and the sensing cuff 73. The cuff structure 6 is fixed to the inner surface of the curler 5.

The pressing cuff 71 is an example of a cuff. The pressing cuff 71 is fluidly connected to the pump 14 via the flow path portion 15. The pressing cuff 71 inflates and presses the back plate 72 and the sensing cuff 73 against the living body. The pressing cuff 71 comprises a plurality of air bags 81, a tube 82 that communicates with the air bags 81, and a connecting portion 83 provided at the tip of the tube 82.

The air bag 81 is a bag-shaped structure. Since the blood pressure measurement device 1 of the present embodiment is configured to use air supplied by the pump 14, a description will be given of the air bag. Where a fluid other than air is used, the bag-shaped structure may be a fluid bag such as a liquid bag.

The plurality of air bags 81 are stacked and fluidly communicate with each other in the stacking direction. In a specific example, the pressing cuff 71 includes two-layer air bags 81 that fluidly communicate with each other in the stacking direction, a tube 82 provided at one longitudinal end of one of the air bags 81, and a connecting portion 83 provided at the tip of the tube 82.

The major surface of one of the air bags 81 of the pressing cuff 71 is fixed to the inner surface of the curler 5. For example, the pressing cuff 71 is attached to the inner surface of the curler 5 with a double-sided adhesive tape or with an adhesive agent.

The two-layer air bags 8 have a rectangular shape elongated in one direction. For example, each air bag 81 is formed by combining two sheet members 86 that are elongated in one direction and welding the edges by heat. In a specific example, as shown in FIGS. 11 to 13, the two-layer air bags 81 includes, from the living body side, a first sheet member 86a, a second sheet member 86b forming the first layer air bag 81 together with the first sheet member 86a, a third sheet member 86c integrally adhered to the second sheet member 86b, and a fourth sheet member 86d forming the second layer air bag 81 together with the third sheet member 86c.

The first sheet member 86a and the second sheet member 86b form the air bag 81 by welding the peripheral portions of the four sides. The second sheet member 86b and the third sheet member 86c are arranged to face each other, and respectively include a plurality of openings 86b1 and 86c1 that fluidly connect the two air bags 81. An adhesive layer or a double-sided adhesive tape is provided on the curler 5 side outer surface of the fourth sheet member 86d, and the fourth sheet member 86d is adhered to the curler 5 with the adhesive layer or with the double-sided adhesive tape.

The third sheet member 86c and the fourth sheet member 86d form the air bag 81 by welding the peripheral portions of the four sides. Further, for example, a tube 82 that is fluidly continuous with the internal space of the air bag 81 is arranged on one side of the third sheet member 86c and the fourth sheet member 86d, and is fixed by welding. For example, the third sheet member 86c and the fourth sheet member 86d form the air bag 81 by welding the peripheral portions of the four sides, with the tube 82 arranged between the third sheet member 86c and the fourth sheet member 86d. By doing so, the tube 82 is integrally welded.

The tube 82 is connected to one of the two-layer air bags 81 and is provided at one longitudinal end of that air bag 81. In a specific example, the tube 82 is provided on the curler 5 side of the two-layer air bags 81 and at the end close to the device body 3. The tube 82 has a connecting portion 83 at the tip. The tube 82 constitutes a flow path between the device body 3 and the air bag 81 in the fluid circuit 7. The connecting portion 83 is connected to the connected portion 34a of the flow path cover 34. The connecting portion 83 is, for example, a nipple.

The back plate 72 is adhered to the outer surface 86a1 of the first sheet member 86a of the pressing cuff 71 with an adhesive layer, a double-sided adhesive tape, or the like. The back plate 72 is formed of a resin material and has a plate shape. For example, the back plate 72 is formed of polypropylene and is formed as a plate shape having a thickness of approximately 1 mm. The back plate 72 has a shape following property.

The shape-following property mentioned here refers to a function in which the back plate 72 can be deformed in conformity with the shape of the contacted portion of the wrist 100, and the contacted portion of the wrist 100 is a portion that is brought into contact with the back plate 72. The contact mentioned here includes both direct contact and indirect contact.

Therefore, the shape-following property means that the back plate 72 provided on the pressing cuff 71 or the back plate 72 provided between the pressing cuff 71 and the sensing cuff 73 is deformable such that the back plate 72 itself or the sensing cuff 73 provided on the back plate 72 is deformable in conformity with the wrist 100 and comes into tight contact with the wrist 100.

For example, the back plate 72 has a plurality of grooves 72a on both major surfaces of the back plate 72 at opposing positions that are at equal intervals in the longitudinal direction of the back plate 72. Since the back plate 72 is thinner at portions where the grooves 72a are provided than at portions where no grooves are provided, the portions where the grooves 72a are provided are easily deformable. Thus, the back plate 72 has a shape-following property that deforms in accordance with the shape of the wrist 100. The back plate 72 has a length that covers the palm side of the wrist 100. The back plate 72 transmits a pressing force from the pressing cuff 71 to the back plate 72 side major surface of the sensing cuff 73 while conforming to the shape of the wrist 100.

The sensing cuff 73 is fixed to the living body side major surface of the back plate 72. As shown in FIG. 12, the sensing cuff 73 is brought into direct contact with that region of the wrist 100 where the artery exists. The sensing cuff 73 is formed to have the same shape as the back plate 72 or to have a shape smaller than the back plate 72, when it is viewed in the longitudinal direction and the width direction of the back plate 72. When the sensing cuff 73 is inflated, the sensing cuff 73 compresses the region where the palm side artery 110 of the wrist 100 exists. The sensing cuff 73 is pressed against the living body by the inflated pressing cuff 71, with the back plate 72 interposed.

In a specific example, the sensing cuff 73 comprises one air bag 91, a tube 92 that communicates with the air bag 91, and a connecting portion 93 provided at the tip of the tube 92. The sensing cuff 73 has one major surface of the air bag 91 fixed to the back plate 72. For example, the sensing cuff 73 is attached to the living body side major surface of the back plate 72 with a double-sided adhesive tape, an adhesive layer, or the like.

The air bag 91 is a bag-shaped structure. Since the blood pressure measurement device 1 of the present embodiment is configured to use air supplied by the pump 14, a description will be given of the air bag. Where a fluid other than air is used, the bag-shaped structure may be a liquid bag or the like. A plurality of air bags 91 are stacked and fluidly communicate with each other in the stacking direction.

The air bag 91 has a rectangular shape elongated in one direction. For example, each air bag 91 is formed by combining two sheet members that are elongated in one direction and welding the edges by heat. In a specific example, as shown in FIGS. 12 and 13, the air bag 91 includes, from the living body side, a fifth sheet member 96a and a sixth sheet member 96b.

For example, a tube 92 that is fluidly continuous with the internal space of the air bag 91 is arranged on one side of the fifth sheet member 96a and the sixth sheet member 96b, and the fifth sheet member 96a and the sixth sheet member 96b are fixed by welding. For example, the fifth sheet member 96a and the sixth sheet member 96b form the air bag 91 by welding the peripheral portions of the four sides, with the tube 92 arranged between the fifth sheet member 96a and the sixth sheet member 96b. By doing so, the tube 92 is integrally welded.

The tube 92 is provided at one longitudinal end of the air bag 91. In a specific example, the tube 92 is provided at that end of the air bag 91 which is closer to the device body 3. The tube 92 has a connecting portion 93 at the tip. The tube 92 constitutes a flow path between the device body 3 and the air bag 91 in the fluid circuit 7. The connecting portion 93 is connected to the connected portion 34a of the flow path cover 34. The connecting portion 93 is, for example, a nipple.

The sheet members 86 and 96 forming the pressing cuff 71 and the sensing cuff 73 are made of a thermoplastic elastomer. Examples of the thermoplastic elastomer with which the sheet members 86 and 96 are formed include thermoplastic polyurethane resin (Thermoplastic PolyUrethane, hereinafter referred to as TPU), vinyl chloride resin (PolyVinyl Chloride), ethylene vinyl acetate resin (Ethylene-Vinyl Acetate), thermoplastic polystyrene resin (Thermoplastic PolyStyrene), thermoplastic polyolefin resin (Thermoplastic PolyOlefin), thermoplastic polyester resin (ThermoPlastic Polyester), and thermoplastic polyamide resin (Thermoplastic PolyAmide). TPU is preferably used as the thermoplastic elastomer. The sheet members may have a single-layer structure or a multi-layer structure.

The sheet members 86 and 96 are not limited to the thermoplastic elastomer, and may be a thermosetting elastomer such as silicone. Further, a combination of a thermoplastic elastomer (for example, TPU) and a thermosetting elastomer (for example, silicone) may be used.

Where the sheet members 86 and 96 are formed of a thermoplastic elastomer, a molding method such as T-die extrusion molding or injection molding is used. Where they are formed of a thermosetting elastomer, a molding method such as mold casting molding is used. After the sheet members are formed by the molding methods, they are sized to a predetermined shape, and the sized pieces are joined by adhesion, welding, or the like, to form bag-shaped structure 81 and 91. Where a thermoplastic elastomer is used, a high frequency welder or laser welding is used as a joining method. Where a thermosetting elastomer is used, a molecular adhesive agent is used.

The fluid circuit 7 is constituted by the case 11, the pump 14, the flow path portion 15, the on-off valves 16, the pressure sensors 17, the pressing cuff 71, and the sensing cuff 73. A specific example of the fluid circuit 7 will be described, with the two on-off valves 16 of the fluid circuit 7 being referred to as a first on-off valve 16A and a second on-off valve 16B, and with the two pressure sensors 17 being referred to as a first pressure sensor 17A and a second pressure sensor 17B.

As shown in FIG. 4, the fluid circuit 7 includes a first flow path 7a that connects the pump 14 to the pressing cuff 71, a second flow path 7b that branches from an intermediate portion of the first flow path 7a and that connects the pump 14 to the sensing cuff 73, and a third flow path 7c that connects the first flow path 7a to the atmosphere. The first flow path 7a includes a first pressure sensor 17A. The first on-off valve 16A is provided between the first flow path 7a and the second flow path 7b. The second flow path 7b includes a second pressure sensor 17B. The second on-off valve 16B is provided between the first flow path 7a and the third flow path 7c.

In the fluid circuit 7 mentioned above, when the first on-off valve 16A and the second on-off valve 16B are closed, only the first flow path 7a is connected to the pump 14, and the pump 14 and the pressing cuff 71 are fluidly connected. In the fluid circuit 7, when the first on-off valve 16A is opened and the second on-off valve 16B is closed, the first flow path 7a and the second flow path 7b are connected, so that the pump 14 and the pressing cuff 71 are fluidly connected and the pump 14 and the sensing cuff 73 are fluidly connected. In the fluid circuit 7, when the first on-off valve 16A is closed and the second on-off valve 16B is opened, the first flow path 7a and the third flow path 7c are connected, so that the pressing cuff 71 and the atmosphere are fluidly connected. In the fluid circuit 7, when the first on-off valve 16A and the second on-off valve 16B are opened, the first flow path 7a, the second flow path 7b and the third flow path 7c are connected, so that the pressing cuff 71, the sensing cuff 73 and the atmosphere are fluidly connected.

Figure 16:
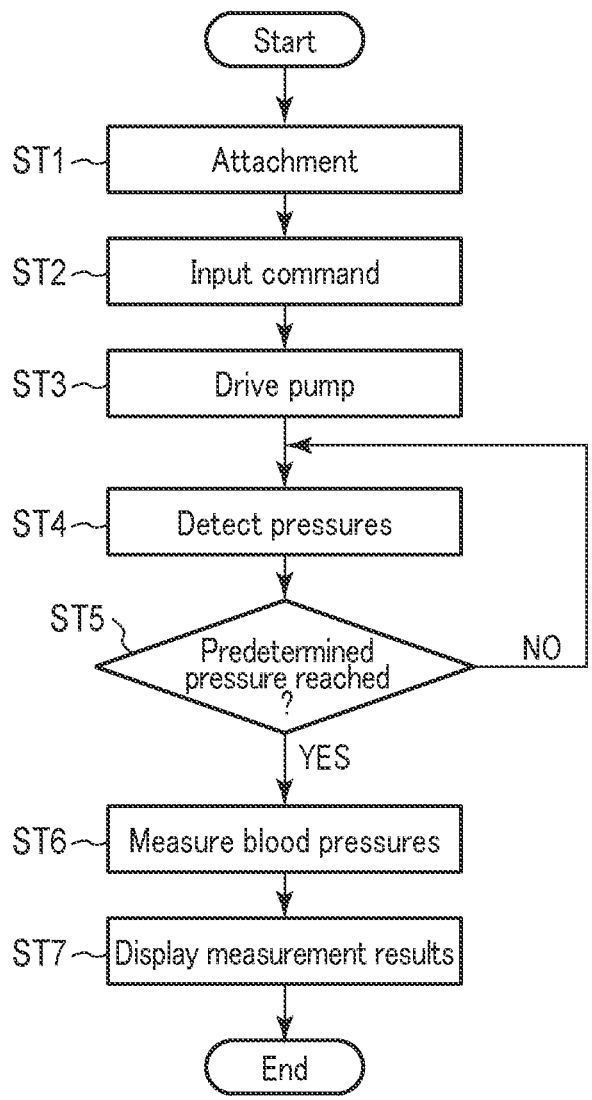
FIG. 16 is a flowchart illustrating an example of how the blood pressure measurement device is used.
Figure 17:
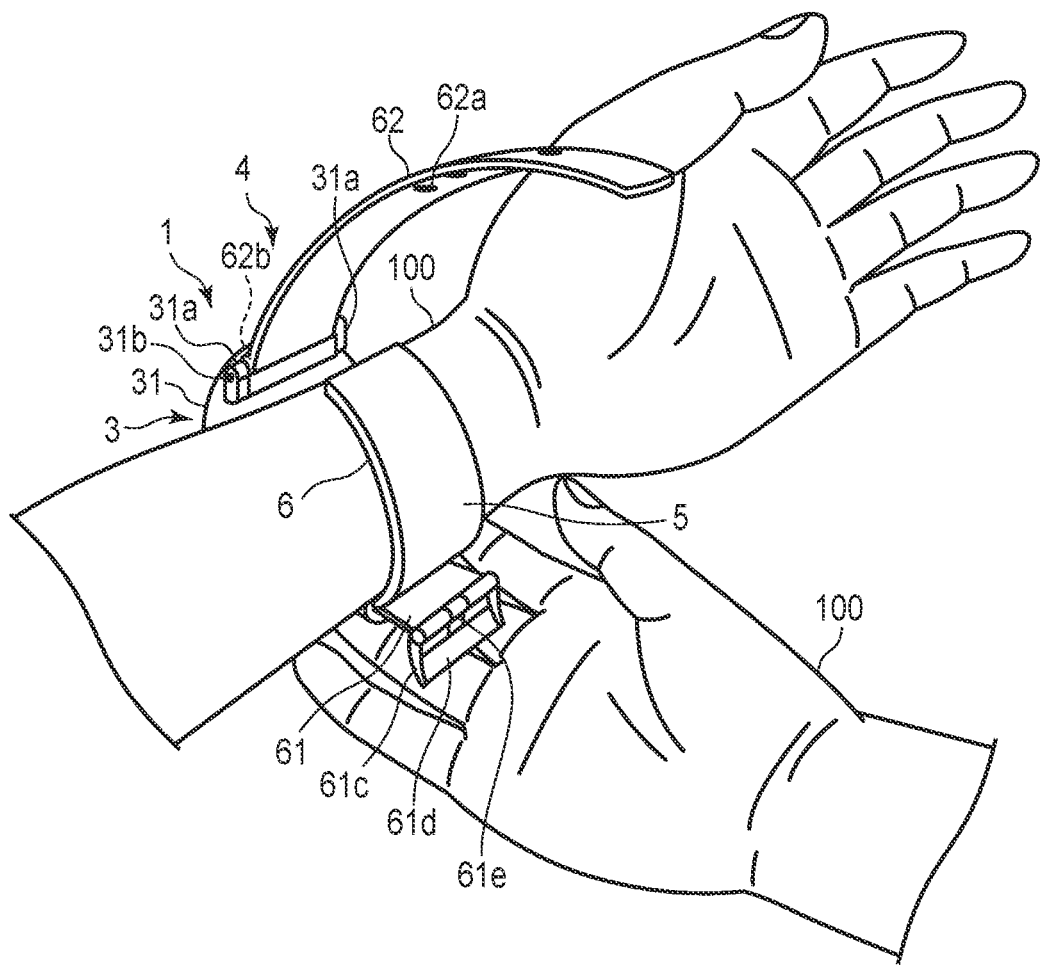
FIG. 17 is a perspective view showing an example of how the blood pressure measurement device is wrapped around the wrist.
Figure 18:
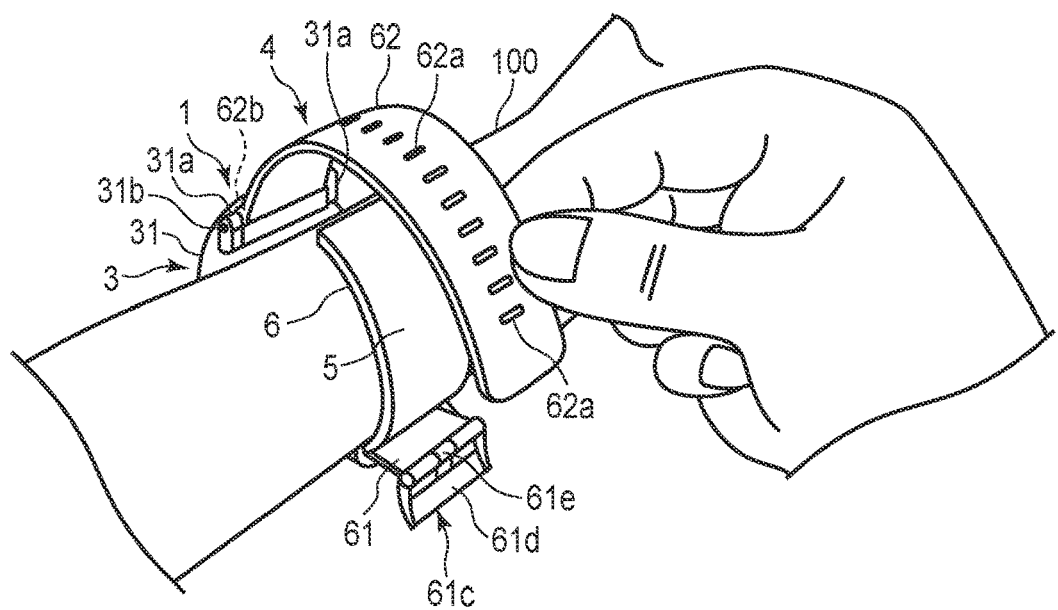
FIG. 18 is a perspective view showing an example of how the blood pressure measurement device is wrapped around the wrist.
Figure 19:
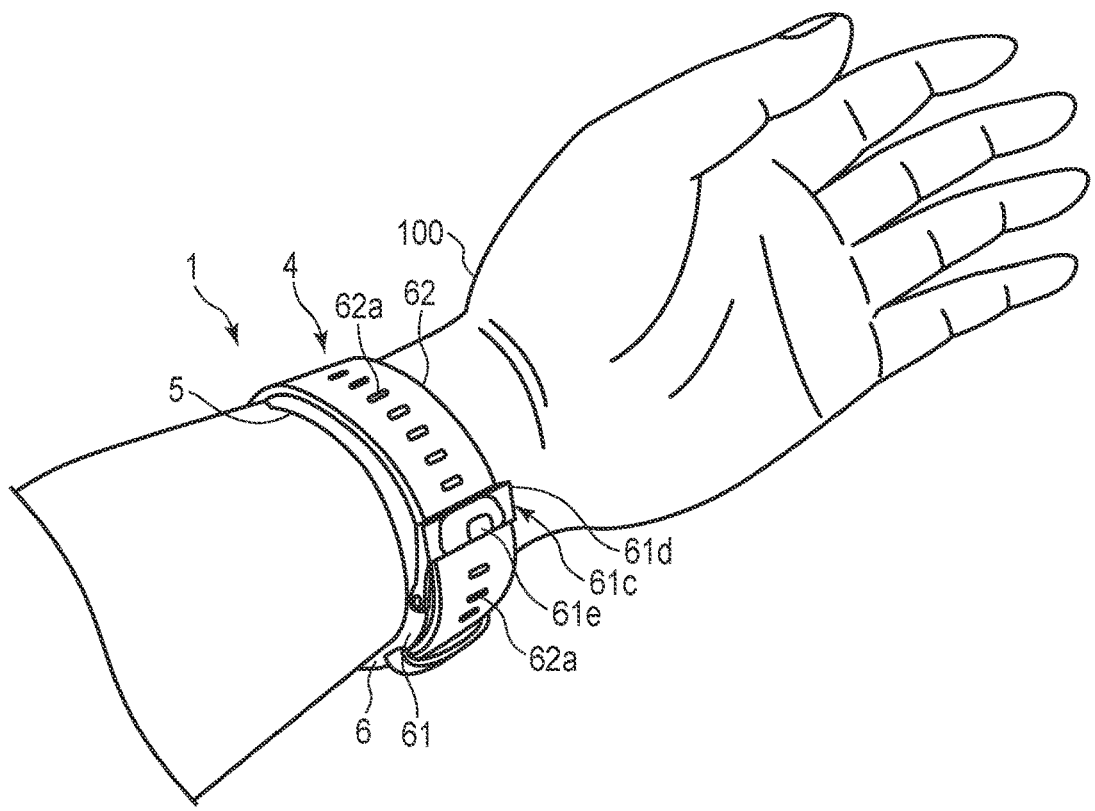
FIG. 19 is a perspective view showing an example of how the blood pressure measurement device is wrapped around the wrist.

Next, an example of how a blood pressure value is measured by the blood pressure measurement device 1 will be described with reference to FIGS. 16 to 19. FIG. 16 is a flowchart showing an example of blood pressure measurement using the blood pressure measurement device 1, and illustrates both the movement of a user and the operation of the control unit 55. FIGS. 17 to 19 show an example in which the user wears the blood pressure measurement device 1 on the wrist 100.

First, the user attaches the blood pressure measurement device 1 to the wrist 100 (step ST1). Specifically, for example, the user inserts one of the wrists 100 into the curler 5, as shown in FIG. 17.

At the time, in the blood pressure measurement device 1, the device body 3 and the sensing cuff 73 are at opposing positions of the curler 5, so that the sensing cuff 73 is arranged in the region where the palm side artery 110 of the wrist 100 exists. As a result, the device body 3 is arranged on the back side of the wrist 100. Next, as shown in FIG. 18, the user passes the second strap 62 through the frame-shaped body 61d of the buckle 61c of the first strap 61, using the hand different from the hand on which the blood pressure measurement device 1 is worn. Next, the user pulls the second strap 62 to bring the member on the inner peripheral surface side of the curler 5, that is, the cuff structure 6, into close contact with the wrist 100, and inserts the stick 61e in a small hole 62a. Thus, as shown in FIG. 19, the first strap 61 and the second strap 62 are connected, and the blood pressure measurement device 1 is attached to the wrist 100.

Next, the user operates the buttons 41 and touch panel 43 of the operation unit 13 to input a command corresponding to the start of blood pressure measurement. In response to the command input operation, the operation unit 13 outputs an electric signal corresponding to the start of measurement to the control unit 55 (step ST2). Upon reception of the electric signal, the control unit 55 drives the vibration motor 19. When the vibration motor 19 is driven, vibration is generated. This vibration is transmitted to the user via the case 11. By this vibration, the user recognizes the start of measurement. Upon receipt of the electric signal, the control unit 55 opens the first on-off valve 16A, closes the second on-off valve 16B, and drives the pump 14, so that compressed air is supplied to the pressing cuff 71 and the sensing cuff 73 via the first flow path 7a and the second flow path 7b (step ST3). As a result, the pressing cuff 71 and the sensing cuff 73 start to inflate.

The first pressure sensor 17A and the second pressure sensor 17B detect the pressures of the pressing cuff 71 and the sensing cuff 73, respectively, and output electric signals corresponding to the pressures to the control unit 55 (step ST4). Based on the received electric signals, the control unit 55 determines whether or not the pressures in the internal spaces of the pressing cuff 71 and sensing cuff 73 can reach a predetermined pressure for blood pressure measurement (step ST5). For example, if the internal pressure of the pressing cuff 71 has not reached the predetermined pressure and the internal pressure of the sensing cuff 73 has reached the predetermined pressure, then the control unit 55 closes the first on-off valve 16A and supplies compressed air through the flow path 7a.

When both the internal pressure of the pressing cuff 71 and the internal pressure of the sensing cuff 73 have reached the predetermined pressure, the control unit 55 stops driving the pump 14 (YES in step ST5). At the time, as shown in FIG. 14, the pressing cuff 71 is sufficiently inflated, and the inflated pressing cuff 71 presses the wrist 100 and the back plate 72. The pressing cuff 71 may be wrinkled along the guide portion 84.

Further, the sensing cuff 73 is supplied with a predetermined amount of air so that the internal pressure becomes the pressure required for blood pressure measurement, and is thus inflated, and the back plate 72 pressed by the pressing cuff 71 presses the sensing cuff 73 against the wrist 100. Therefore, the sensing cuff 73 pushes the artery 110 in the wrist 100 and presses the artery 110 as shown in FIG. 15.

In addition, the control unit 55 controls the second on-off valve 16B to repeatedly open and close the second on-off valve 16B, or adjusts the opening of the second on-off valve 16B, such that the pressure in the internal space of the pressing cuff 71 is decreased. In the process of this pressure decrease, the control unit 55 obtains measurement results, such as blood pressure values, e.g., systolic blood pressure and diastolic blood pressure, a heart rate or the like, based on the electric signals output from the second pressure sensor 17B.

The timing at which the first on-off valve 16A and the second on-off valve 16B are opened and closed during blood pressure measurement can be determined as appropriate. Although a description was given referring to an example in which the control unit 55 calculates blood pressure in the pressure increasing process of the pressing cuff 71, the blood pressure may be calculated in the pressure decreasing process of the pressing cuff 71 or may be calculated in both the pressure increasing process and the pressure decreasing process of the pressing cuff 71. Next, the control unit 55 outputs image signals corresponding to the obtained measurement results to the display unit 12.

Upon receipt of the image signals, the display unit 12 displays the measurement results on the screen. The user confirms the measurement results by looking at the display unit 12. After the measurement, the user removes the stick 61e from the small hole 62a, removes the second strap 62 from the frame-shaped body 61d, and pulls the wrist 100 off the curler 5, thereby detaching the blood pressure measurement device 1 from the wrist 100.

In the blood pressure measurement device 1 according to the embodiment configured as described above, vibration is generated by the buttons 41 or the vibration motor 19 when the operation unit 13 is operated or when the operation start is notified by the vibration motor 19. In the blood pressure measurement device 1, however, part of the operation unit 13, i.e., an example of the drive unit, and the vibration motor 19 are provided on one side of the pump 14 as viewed in the orthogonal direction V2, and the packing 35, the on-off valves 16 and the pressure sensors 17 are located on the opposite side of the base 33, with the pump 14 interposed.

For this reason, the packing 35, the on-off valves 16, and the pressure sensors 17 can be arranged at positions far from the buttons 41 and the vibration motor 19, so that the vibration generated by the buttons 41 and the vibration motor 19 is not easily transmitted to the packing 35, the on-off valve 16 or the vibration motor 19. Further, part of the operation unit and the vibration motor 19 are provided at positions far from the on-off valves 16 and the pressure sensors 17. Still further, the packing 35 absorbs the vibration of the base 33 generated when the vibration motor is driven and also absorbs the strain caused in the base 33 when the operation unit 13 is operated.

Furthermore, since the base 33 has the pump housing portion 33c including the first rib 33c1, the second rib 33c2, the third rib 33c3 and the fourth rib 33c4, the strength of the base 33 can be improved. By improving the strength of the base 33, the strain in the base 33 which may be caused by the operation of the buttons 41 can be reduced. Furthermore, the ribs of the base 33 include the first rib 33c1 and second rib 33c2 extending in the orthogonal direction V2. Therefore, the strength of the base 33 is improved in the orthogonal direction V2. Thus, the buckling strength of the base 33 is improved in the pushing directions of the buttons 41, so that the adverse effect of the strain in the base 33 which may be caused by the operation of the buttons 41 can be reduced.

Furthermore, since the pump housing portion 33c is formed to have a frame shape, the strength of the pump housing portion 33c can be improved, and thus the strength of the base 33 can be improved.

Furthermore, the pump 14 is fixed to the base 33 by means of the double-sided adhesive tape 14c. With this configuration, the double-sided adhesive tape 14c can absorb the vibration and strain generated in the base 33.

Furthermore, the pump 14 has a pump base portion 14a made of a metal plate. With this configuration, the base 33 is reinforced by the pump base portion 14a, so that the strength of the base 33 can be improved.

Furthermore, part of the fluid circuit 7 is in the base 33, so that the blood pressure measurement device 1 can be reduced in size.

As described above, in the blood pressure measurement device 1 according to the embodiment, the adverse effect of the vibration and the adverse effect of the strain generated in the base 33 can be reduced.

In the present embodiment, the device body 3 is arranged on the back side of the wrist 100, but the device body 3 may be arranged on the palm side of the wrist 100. That is, the device body 3 may be fixed to the outer surface of the region of the curler 5 where the sensing cuff 73 is arranged. In the blood pressure measurement device 1 having this configuration, since the device body 3 is arranged on the palm side and is thus arranged in the region where the artery of the wrist 100 exists, the distance to the sensing cuff 73 is short, and the tube 92 provided for the sensing cuff 73 can be short.

Figure 20:
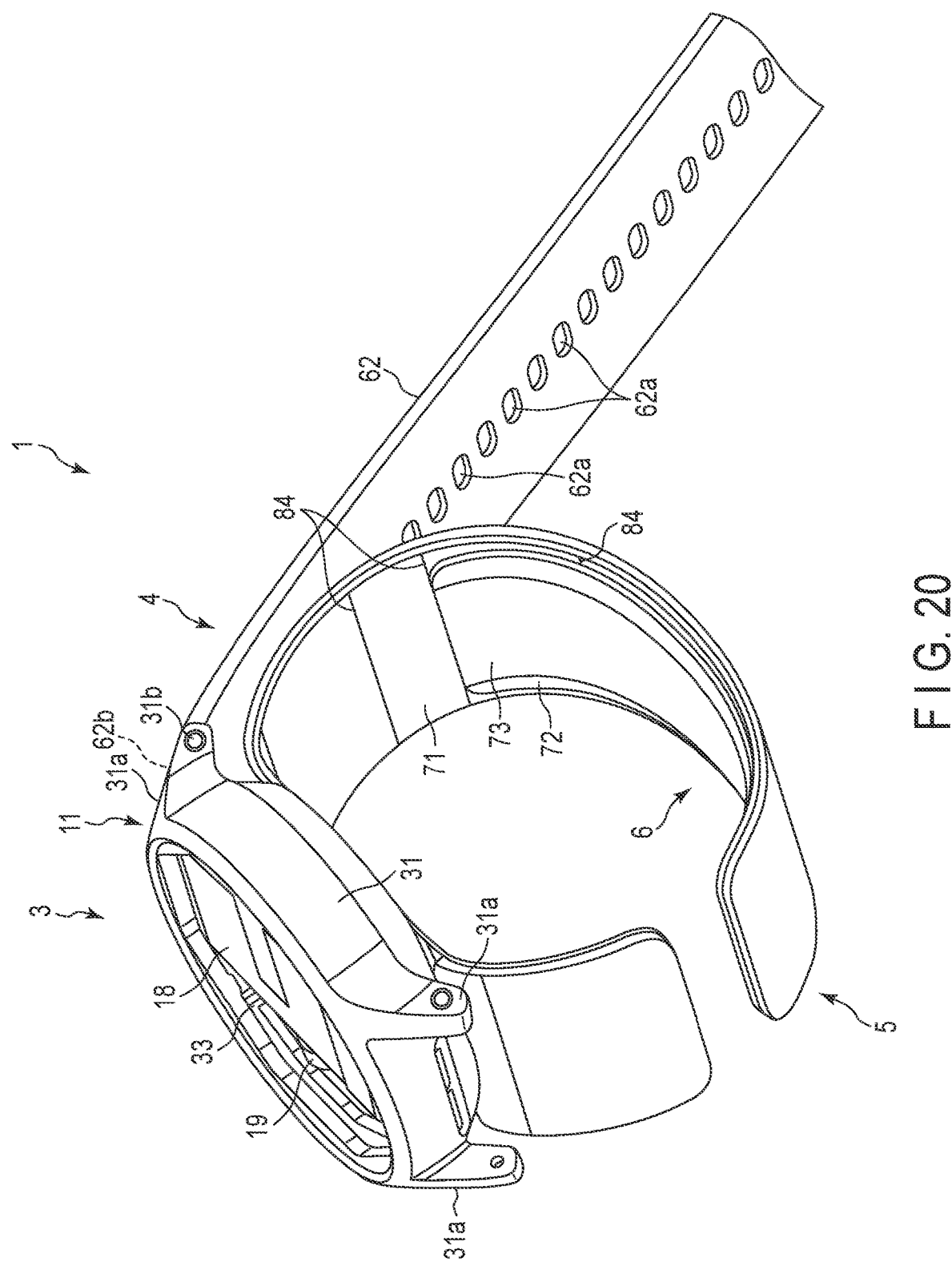
FIG. 20 is a perspective view showing another configuration of the blood pressure measurement device.

In the present embodiment, the curler 5 is configured such that one end is fixed between the base 33 of the device body 3, the flow path cover 34 and the back cover 36, and the other end is arranged close to the device body 3. As shown in FIG. 20, however, the curler 5 may be fixed to the outer surface of the back cover 36 such that its one end is projected from one pair of lugs 31a of the back cover 36 and the other end is projected from the other pair of lugs 31a and extended to a position adjacent to the one end.

The above-described embodiment is merely an example of the present invention in all respects. Needless to say, various improvements and modifications can be made without departing from the scope of the present invention. That is, in implementing the present invention, a specific configuration according to the embodiment may be adopted as appropriate.

REFERENCE SIGNS LIST

1 . . . Blood Pressure Measurement Device
3 . . . Device Body
4 . . . Strap
5 . . . Curler
6 . . . Cuff Structure
7 . . . Fluid Circuit
7a . . . First Flow Path
7b . . . Second Flow Path
7c . . . Third Flow Path
11 . . . Case
12 . . . Display Unit
13 . . . Operation Unit
14 . . . Pump
14a . . . Pump Base Portion
14b . . . Pump Body
14c . . . Double-Sided Adhesive Tape
15 . . . Flow Path Portion
16 . . . On-Off Valve
16A . . . First On-Off Valve
16B . . . Second On-Off Valve
17 . . . Pressure Sensor
17A . . . First Pressure Sensor
17B . . . Second Pressure Sensor
18 . . . Power Supply Unit
19 . . . Vibration Motor
20 . . . Control Board
31 . . . Outer Case
31a . . . Lug
31b . . . Spring Rod
31c . . . Hole
32 . . . Windshield
33 . . . Base
34a . . . Sensor Support Portion
33b . . . Surface
33c . . . Pump Housing Portion
33c1 . . . First Rib
33c2 . . . Second Rib
33c3 . . . Third Rib
33c4 . . . Fourth Rib
33c5 . . . Hole
33d . . . Attachment Portion
33d1 . . . First Hole
33d2 . . . Second Hole
33d3 . . . Third Hole
33d4 . . . Fourth Hole
34a . . . Connected Portion
35 . . . Back Cover
35 . . . Packing 35a ... First Nozzle
35b ... Second Nozzle
35c ... Third Nozzle
35d ... Fourth Nozzle
35e ... First Recess
35f ... Second Recess
35g ... Third Recess
35h ... Fourth Recess
36 ... Back Cover
36a ... Screw
37 ... Flow Path Tube
41 ... Button
42 ... Sensor
43 ... Touch Panel
51 ... Board
52 ... Acceleration Sensor
53 ... Communication Unit
54 ... Storage Unit
55 ... Control Unit
61 ... First Strap
61a ... First Hole Portion
61b ... Second Hole Portion
61c ... Buckle
61d ... Frame-Shaped Body
61e ... Stick
62 ... Second Strap
62a ... Small Hole
71 ... Pressing Cuff
72 ... Back Plate
72a ... Groove
73 ... Sensing Cuff
81 ... Bag-Shaped Structure
81 ... Air Bag
82 ... Tube
83 ... Connecting Portion
86 ... Sheet Member
86a ... First Sheet Member
86a1 ... Outer Surface
86b ... Second Sheet Member
86b1 ... Opening
86c ... Third Sheet Member
86c1 ... Opening
86d ... Fourth Sheet Member
91 ... Bag-Shaped Structure
91 ... Air Bag
92 ... Tube
93 ... Connecting Portion
96 ... Sheet Member
96a ... Fifth Sheet Member
96b ... Sixth Sheet Member
100 ... Wrist
110 ... Artery

The invention claimed is:

1. A blood pressure measurement device comprising:
an outer case;
a base housed in the outer case;
a pump provided on the base such that the pump is shifted from a center of the outer case and located on one side as viewed in a circumferential direction of a wrist of a living body;
a drive unit provided on the base such that the drive unit is located on one side of the pump as viewed in a direction orthogonal to the circumferential direction;
an on-off valve provided on the base such that the on-off valve is located on another side of the pump as viewed in the direction orthogonal to the circumferential direction;
a pressure sensor provided on the base such that the pressure sensor is located on said another side of the pump as viewed in the direction orthogonal to the circumferential direction; and
packing formed of an elastic body and provided between the on-off valve and the pressure sensor and the base, wherein
the packing comprises a plurality of recesses in which the on-off valve and the pressure sensor are housed, and
the packing is provided between the on-off valve and the pressure sensor housed in the recesses and the base.

2. The blood pressure measurement device according to claim 1, wherein the base includes a rib provided between the drive unit and the packing and extending in the direction orthogonal to the circumferential direction.

3. The blood pressure measurement device according to claim 2, wherein the base includes a pump housing portion that houses the pump and that is partly constituted by the rib.

4. The blood pressure measurement device according to claim 1, wherein the pump is fixed to the base by means of a double-sided adhesive tape.

5. The blood pressure measurement device according to claim 1, wherein the pump includes a pump base made of a metal plate, and a pump body.

6. The blood pressure measurement device according to claim 1, wherein the packing is interposed between the on-off valve and the pressure sensor.

7. The blood pressure measurement device according to claim 1, wherein the packing has a rectangular parallelepiped shape.

8. The blood pressure measurement device according to claim 1, wherein the on-off valve and the pressure sensor are housed in separate recesses of the plurality of recesses.

* * * * *